(12) United States Patent
Zachar et al.

(10) Patent No.: US 11,992,615 B2
(45) Date of Patent: *May 28, 2024

(54) CLOSED SUCTION SYSTEM

(71) Applicant: Airway Medix S.A., Warsaw (PL)

(72) Inventors: Oron Zachar, Tel Aviv (IL); Yair Ramot, Kfar Maas (IL); Eizik Amar, Ashdod (IL)

(73) Assignee: AIRWAY MEDIX S.A., Warsaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 17/951,151

(22) Filed: Sep. 23, 2022

(65) Prior Publication Data

US 2023/0256183 A1 Aug. 17, 2023

Related U.S. Application Data

(63) Continuation of application No. 16/073,326, filed as application No. PCT/IL2016/051367 on Dec. 22, (Continued)

(30) Foreign Application Priority Data

Jan. 6, 2016 (GB) ..................................... 1600233

(51) Int. Cl.
*A61M 16/04* (2006.01)
*A61M 1/00* (2006.01)
(Continued)

(52) U.S. Cl.
CPC ...... *A61M 16/0463* (2013.01); *A61M 1/7413* (2021.05); *A61M 16/00* (2013.01); (Continued)

(58) Field of Classification Search
CPC .... A61M 1/0035; A61M 1/00; A61M 1/0041; A61M 1/0043; A61M 16/00; (Continued)

(56) References Cited

U.S. PATENT DOCUMENTS 10,016,575 B2 * 7/2018 Vazales ............. A61M 25/1002
10,926,009 B2 * 2/2021 Zachar ................ A61M 1/7413
(Continued)

FOREIGN PATENT DOCUMENTS

GB           2117245 A  * 10/1983  .......... A61M 1/0064
WO    WO-2009019538 A1 *  2/2009  .......... A61M 1/0043

*Primary Examiner* — Tu A Vo
(74) *Attorney, Agent, or Firm* — Browdy and Neimark, PLLC

(57) ABSTRACT

A cleaning catheter (200) insertable into a tracheal ventilation tube (160) and an input module (156) are provided for use with a suction source (601), the input module (156) coupled to the cleaning catheter (200) and including (i) an inflation module (330), including an inflation chamber (335) separate from the suction source (601); (ii) a flow regulator (700), configured to assume first and second fluid-control states; and (iii) a mechanical user control element (320), which is configured (a) to mechanically and non-electrically set the fluid-control states, (b) to assume first and second configurations, and (c) to mechanically and non-electrically increase pressure in an interior of an inflation chamber (335) during a transition of the mechanical user control element (320) from the first configuration to the second configuration. The flow regulator (700), when in the first fluid-control state connects the suction source (601) and an interior of an inflatable element (588) of the cleaning catheter (200) in fluid communication to deflate the inflatable element (588).

20 Claims, 14 Drawing Sheets

Related U.S. Application Data 2016, now Pat. No. 11,452,831, which is a continuation-in-part of application No. 15/363,782, filed on Nov. 29, 2016, now abandoned.

(60) Provisional application No. 62/319,640, filed on Apr. 7, 2016, provisional application No. 62/287,223, filed on Jan. 26, 2016.

(51) Int. Cl.
| | | |
|---|---|---|
| *A61M 16/00* | (2006.01) | |
| *A61M 25/10* | (2013.01) | |
| *A61M 39/00* | (2006.01) | |
| *A61M 39/22* | (2006.01) | |
| *A61M 25/00* | (2006.01) | |
| *A61M 39/24* | (2006.01) | |

(52) U.S. Cl.
CPC ............ *A61M 25/10* (2013.01); *A61M 39/00* (2013.01); *A61M 1/743* (2021.05); *A61M 2025/0019* (2013.01); *A61M 39/22* (2013.01); *A61M 39/24* (2013.01); *A61M 2205/183* (2013.01); *A61M 2205/581* (2013.01); *A61M 2209/10* (2013.01)

(58) Field of Classification Search
CPC .......... A61M 16/0463; A61M 16/0465; A61M 16/0468; A61M 16/047; A61M 25/10; A61M 2205/581; A61M 2205/183; A61M 16/0472; A61M 16/0475; A61M 16/0477; A61M 16/0479; A61M 16/0481; A61M 16/0484; A61M 16/0486; A61M 16/0427; A61M 16/0434; A61M 16/0445; A61M 16/0447; A61M 16/08; A61M 16/0816; A61M 16/0875; A61M 16/0402; A61M 25/1018; A61M 25/10181; A61M 25/10184; A61M 2025/1086; A61M 39/10; A61M 2039/1066; A61M 2202/0014

See application file for complete search history.

(56) References Cited

U.S. PATENT DOCUMENTS

| | | | |
|---|---|---|---|
| 11,452,831 B2 * | 9/2022 | Zachar | .................. A61M 39/00 |
| 2003/0120203 A1 * | 6/2003 | Guo | ...................... A61M 1/774 |
| | | | 604/35 |
| 2014/0142496 A1 * | 5/2014 | Zachar | .................... A61M 1/76 |
| | | | 604/118 |
| 2014/0150782 A1 * | 6/2014 | Vazales | ............. A61M 25/1018 |
| | | | 128/202.16 |

* cited by examiner

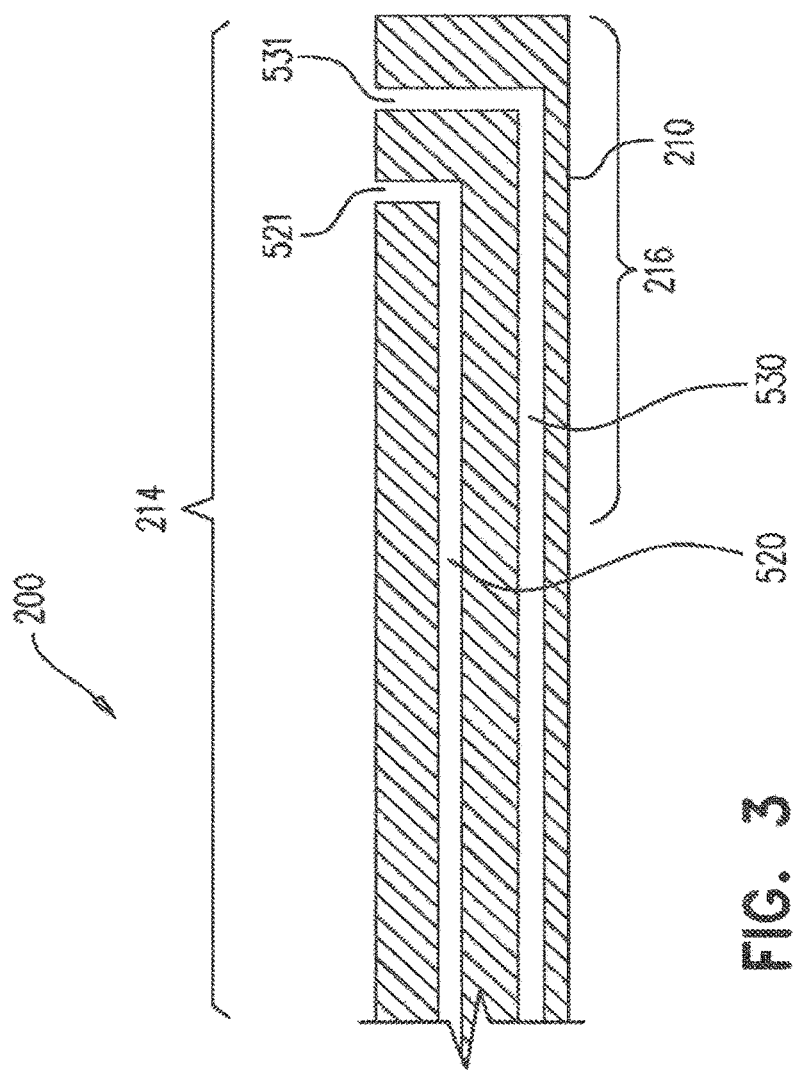
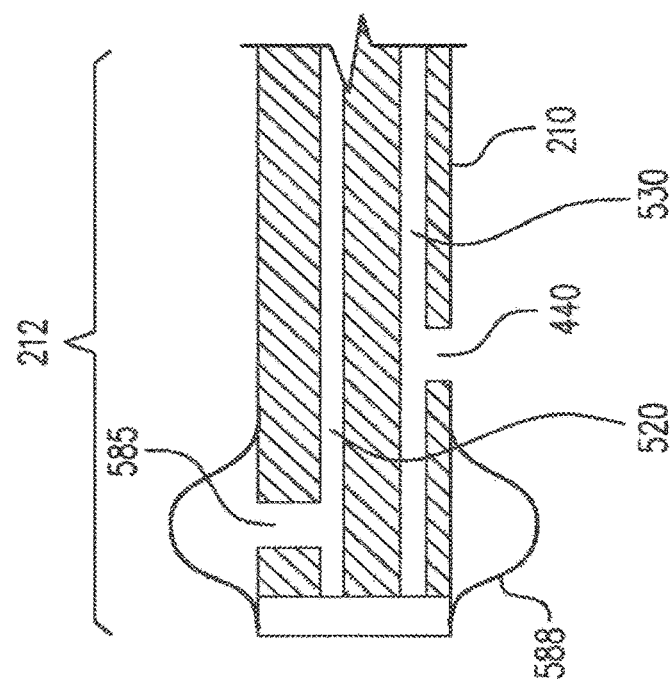
FIG. 3

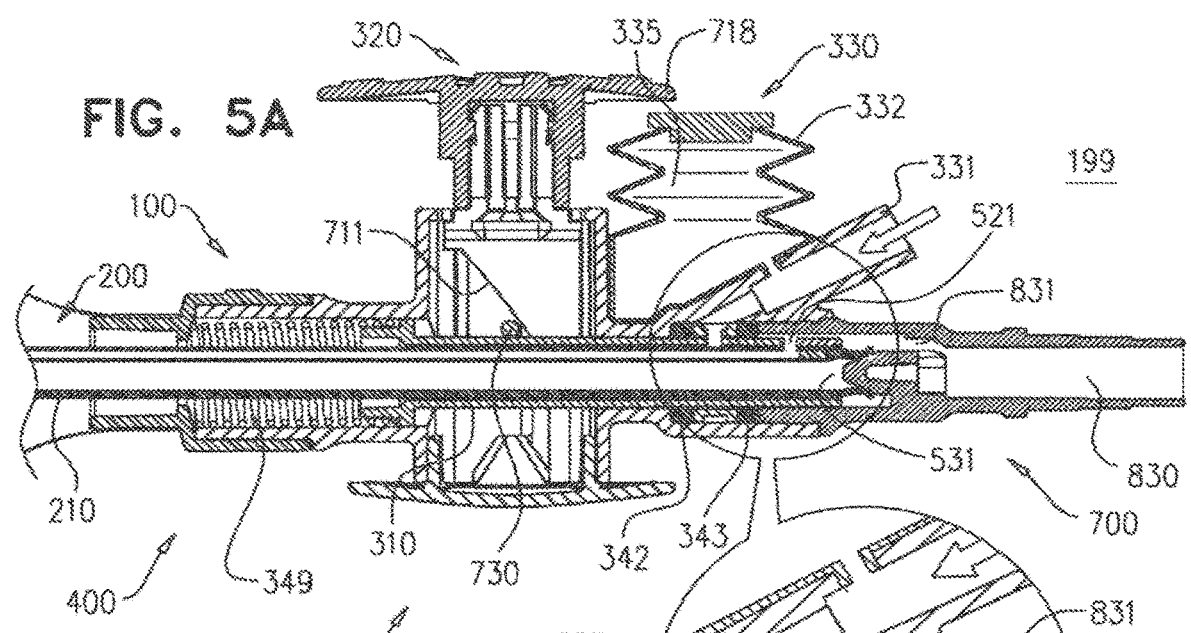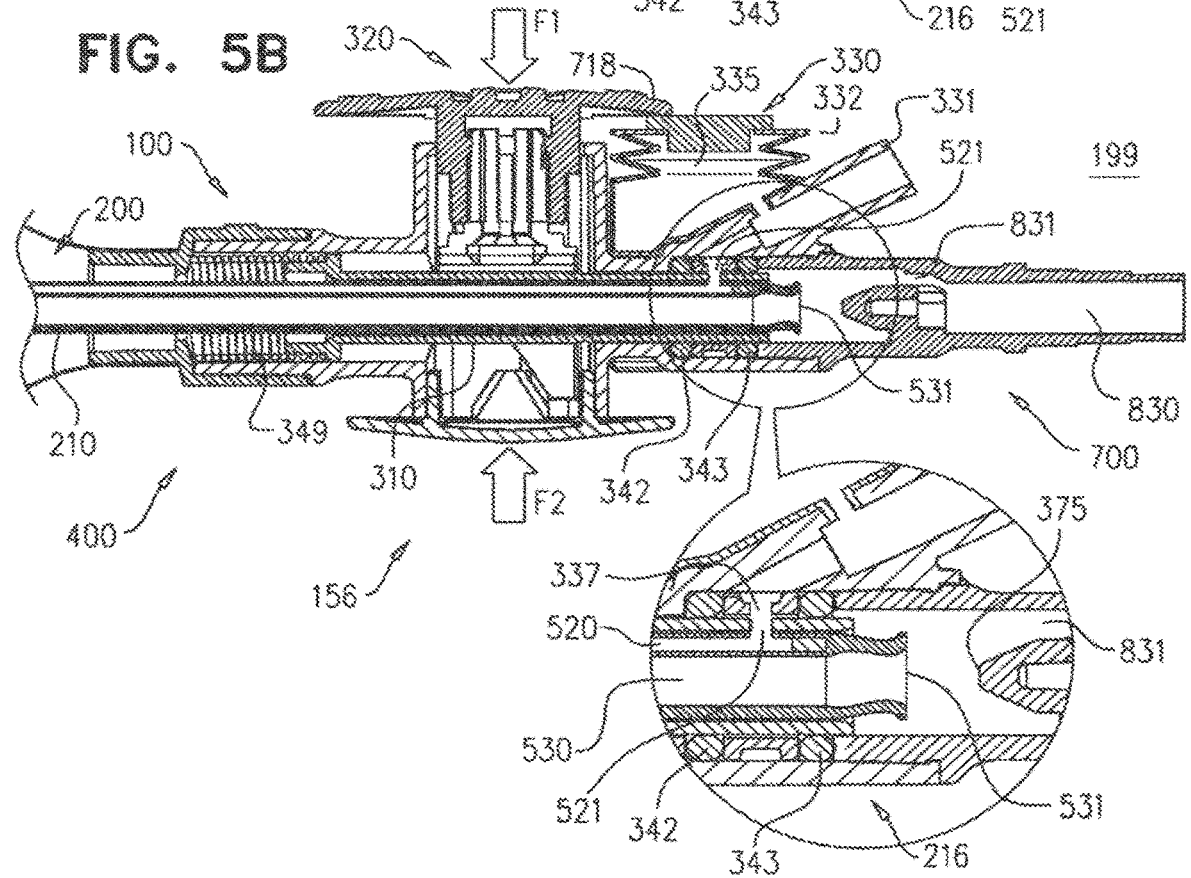

CLOSED SUCTION SYSTEM

CROSS-REFERENCE TO RELATED APPLICATIONS

PCT/IL2016/051367, filed on 22 Dec. 2016: (a) claims priority from (i) U.S. Provisional Application 62/287,223, filed Jan. 26, 2016, (ii) U.S. Provisional Application 62/319,640, filed Apr. 7, 2016, and (iii) UK Application 1600233.9, filed Jan. 6, 2016, and (b) claims priority from and is a continuation-in-part of U.S. application Ser. No. 15/363,782, filed Nov. 29, 2016. All of the above-mentioned applications are assigned to the assignee of the present application and are incorporated herein by reference. PCT/IL2016/051367 is incorporated herein by reference.

FIELD OF THE APPLICATION

The present invention relates generally to medical suction catheter devices, and specifically to catheter devices for aspiration of tracheobronchial secretions and/or cleaning of tracheal ventilation tubes.

BACKGROUND OF THE APPLICATION

Suction catheters are commonly used to aspirate tracheobronchial fluids in patients ventilated with endotracheal tube (ETT) and tracheostomy tube devices. A problematic aspect of the use of suction catheters is the presence of bacterial biofilm within the ETT lumen through which the suction catheter passes. Consequently, as the suction catheter is inserted, there is high risk of it carrying bacterial biofilm from the ETT lumen deeper into the bronchial tree where the suction catheter reaches, and thereby increasing the risk of lung infection. Moreover, buildup of substantial biofilm thickness reduces the effective free lumen of the ETT for air passage. Therefore, there is a need for maintaining cleaner ETT lumens between suction operations, and preventing buildup of significant biofilm thickness.

UK Publication GB 2482618 A to Einav et al., which is assigned to the assignee of the present application and is incorporated herein by reference, describes a multi-lumen catheter for multiple fluids conduction, including balloon inflation with air via an inflation lumen, suction via a suction lumen, and cleaning fluids delivery via a cleaning fluid delivery lumen.

U.S. Pat. No. 8,999,074 to Zachar et al., which is assigned to the assignee of the present application and is incorporated herein by reference, describes a cleaning catheter that includes fluid-delivery and suction lumens. A flow regulator defines suction and fluid ports. A mechanical user control element is configured to mechanically and non-electrically set activation states of the flow regulator, and transition between first and third configurations via a second configuration. When the control element is in the first configuration, the flow regulator blocks fluid communication (a) between the suction port and the suction lumen and (b) between the fluid port and the fluid-delivery lumen. When the control element is in the second configuration, the flow regulator effects fluid communication between the suction port and the suction lumen, and blocks fluid communication between the fluid port and the fluid-delivery lumen. When the control element is in the third configuration, the flow regulator effects fluid communication (a) between the suction port and the suction lumen and (b) between the fluid port and the fluid-delivery lumen.

SUMMARY OF THE APPLICATION

Some applications of the present invention provide a multi-lumen catheter for cleaning an inner surface of a tracheal ventilation tube. Some techniques of the present invention enable single-handed simultaneous activation of inflation of an inflatable element and suctioning in a closed suction system for use with the tracheal ventilation tube. A closed suction system allows catheters to be used repeatedly without being detached from the tube system including the ventilation air supply. Applications of the present invention generally provide simple user control of conduction of fluids under positive and negative pressure (suction).

The cleaning catheter is insertable into the tracheal ventilation tube, and is shaped so as to define one or more distal suction orifices. The cleaning catheter comprises an elongate, flexible, tubular catheter main body, and an inflatable element, which is mounted to the catheter main body, typically at a location within 3 cm of at least one of the one or more distal suction orifices. An input module is coupled to the cleaning catheter, and comprises an inflation module, which comprises an inflation chamber separate from the suction source. The input module also comprises a flow regulator, which (a) is shaped so as to define a suction port coupleable in fluid communication with the suction source, and (b) is configured to assume at least first and second fluid-control states.

The input module further comprises a mechanical user control element, which is configured (a) to mechanically and non-electrically set the fluid-control states of the flow regulator, (b) to assume at least first and second configurations, and (c) to mechanically and non-electrically increase pressure in an interior of the inflation chamber during at least a portion of a transition of the mechanical user control element from the first configuration to the second configuration. The input module is arranged such that
 when the mechanical user control element is in the first configuration, the flow regulator is in the first fluid-control state, in which the flow regulator blocks fluid communication between the suction source and the distal suction orifices, and
 when the mechanical user control element is in the second configuration, the flow regulator is in the second fluid-control state, in which the flow regulator (A) connects the suction source and the distal suction orifices in fluid communication, and (B) connects the interior of the inflation chamber and an interior of the inflatable element in fluid communication to inflate the inflatable element.

As a result of this arrangement, a single mechanical user control element both (a) mechanically creates pressure to inflate the inflation element and (b) mechanically connects the suction source and the distal suction orifices in fluid communication.

In some applications of the present invention, the input module is arranged such that:
 when the mechanical user control element is in the first configuration and the flow regulator is in the first fluid-control state, the flow regulator connects the suction source and the interior of the inflatable element in fluid communication to deflate the inflatable element, and
 when the mechanical user control element is in the second configuration and the flow regulator is in the second fluid-control state, the flow regulator does not connect the suction source and the interior of the inflatable element in fluid communication.

In some applications of the present invention, the fluid-control states are actuated by axial motion of a proximal portion of the catheter main body relative to an input module housing. For some of these applications, transitions between the states are caused by shifts in alignment of lumen inlets with respect to various chambers of the input module. The shifts in alignment are typically caused via axial motion of a proximal-most input portion of the catheter main body within the input module housing, along the longitudinal axes of the input portion and the input module. For some applications, the mechanical user control element comprises a user control handle, the movement of which includes a component perpendicular to the associated axial motion of the catheter main body. The mechanical user control element translates the movement of the user control handle into axial motion of the catheter main body with respect to the input module housing.

In other applications of the present invention, the fluid-control states are not actuated by axial motion of the proximal portion of the catheter main body relative to the input module housing, and the mechanical user control element does not translate the movement of the user control handle into axial motion of the catheter main body relative to the input module housing. Instead, the proximal-most input portion of the catheter main body is fixed with respect to the input module. The movement of the user control handle actuates the fluid-control states without translating the movement into axial motion of the proximal portion of the catheter main body. The input module is arranged such that the user control handle is moveable with respect to the catheter main body in two opposite directions along a movement axis that forms a fixed angle of between 45 and 135 degrees with a central longitudinal axis of the proximal-most input portion of the catheter main body, typically 90 degrees. The input module is arranged such that movement of the user control handle along the movement axis mechanically causes corresponding movement, along or alongside the movement axis, of a distal opening of the suction port, which selectively brings the distal end of the suction port into and out of fluid communication with the interior of the inflatable element and the distal suction orifices.

For some applications, the inflation chamber is disposed within the mechanical user control element; for example, the inflation chamber may be defined by one or more interior surfaces of the user control handle.

In other applications of the present invention, the input module is arranged such that when the mechanical user control element is in the first configuration and the flow regulator is in the first fluid-control state, the flow regulator connects the interior of the inflation chamber and the interior of the inflatable element in fluid communication to deflate the inflatable element.

For cleaning a ventilation tube, the cleaning action typically comprises the following steps, which are typically performed in the following order:
  inserting the cleaning catheter inti the ventilation tube in a proximal to distal direction while the inflatable element (e.g. balloon) is essentially deflated;
  inflating the inflatable element at a location near the distal end of the ventilation tube (typically within 2 cm of the distal end);
  withdrawing the catheter along the ventilation tube in a distal to proximal direction while the inflatable element is inflated and suction is applied to the one or more suction orifices; and
  deflating the inflatable element when the inflatable element is near the proximal end of the ventilation tube or fully outside the proximal end of the ventilation tube.

There is therefore provided, in accordance with an application of the present invention, apparatus for use with a tracheal ventilation tube and a suction source, the apparatus including:
  (A) a cleaning catheter, which (a) is insertable into the ventilation tube, (b) is shaped so as to define one or more distal suction orifices, and (c) which includes:
    (i) an elongate, flexible, tubular catheter main body; and
    (ii) an inflatable element, which is mounted to the catheter main body at a location within 3 cm of at least one of the one or more distal suction orifices; and
  (B) an input module, which is coupled to the cleaning catheter, and includes:
    (i) an inflation module, which includes an inflation chamber separate from the suction source;
    (ii) a flow regulator, which (a) is shaped so as to define a suction port coupleable in fluid communication with the suction source, and (b) is configured to assume at least first and second fluid-control states; and
    (iii) a mechanical user control element, which is configured (a) to mechanically and non-electrically set the fluid-control states of the flow regulator, (b) to assume at least first and second configurations, and (c) to mechanically and non-electrically increase pressure in an interior of the inflation chamber during at least a portion of a transition of the mechanical user control element from the first configuration to the second configuration,
  wherein the input module is arranged such that:
    at least when the mechanical user control element is in the first configuration, the flow regulator is in the first fluid-control state, in which the flow regulator (a) blocks fluid communication between the suction source and the distal suction orifices and (b) connects the suction source and an interior of the inflatable element in fluid communication to deflate the inflatable element,
    at least when the mechanical user control element is in the second configuration, the flow regulator is in the second fluid-control state, in which the flow regulator (a) connects the suction source and the distal suction orifices in fluid communication, (b) connects the interior of the inflation chamber and an interior of the inflatable element in fluid communication to inflate the inflatable element, and (c) does not connect the suction source and the interior of the inflatable element in fluid communication, and
    the flow regulator is (a) not in the first fluid-control state when the mechanical user control element is in the second configuration, and (b) not in the second fluid-control state when the mechanical user control element is in the first configuration.

For some applications, the mechanical user control element is configured to mechanically and non-electrically increase the pressure in the interior of the inflation chamber during an entirely of the transition of the mechanical user control element from the first configuration to the second configuration.

For some applications, the input module is configured such that during the at least a portion of the transition of the mechanical user control element from the first configuration to the second configuration, before the flow regulator assumes the second fluid-control state, a volume of the interior of the inflation chamber decreases by between 10% and 90%.

For some applications, the mechanical user control element is configured to mechanically and non-electrically increase the pressure in the interior of the inflation chamber during motion of the mechanical user control element while the flow regulator is in the second fluid-control state.

For some applications, the suction port is coupled in fluid communication with the suction source.

For some applications, the input module further includes a user signal generator, which is configured to generate a user signal during or upon deflation of the inflatable element.

For some applications, the inflation chamber has a volume of between 1 and 10 cc when the mechanical user control element is in the first configuration.

For some applications, when the mechanical user control element is in the second configuration, the inflation chamber has a volume of at least 1 cc less than when the mechanical user control element is in the first configuration.

For some applications, the mechanical user control element is biased toward the first configuration.

For some applications, the cleaning catheter further includes one or more suction lumens arranged along the catheter main body, and the flow regulator, when in the second fluid-control state, connects in fluid communication the suction source and the distal suction orifices via the one or more suction lumens.

For some applications, the inflatable element includes a balloon.

For some applications, the inflatable element is mounted to the catheter main body is within 5 cm of a distal end of the catheter main body.

For some applications, the inflatable element has a greatest outer diameter of between 6 and 12 mm when inflated at 1 bar above atmospheric pressure and unconstrained.

For some applications, the apparatus is for use with a ventilator, and the apparatus further includes a tube-connector assembly, which is configured to couple the ventilation tube in fluid communication with the ventilator, in a substantially air-tight manner.

For some applications, the first and the second configurations are first and second spatial positions, respectively, and the mechanical user control element is configured to assume at least the first and the second spatial positions.

For some applications, the mechanical user control element is arranged to move between first and second spatial end-points, and the first and the second spatial positions correspond with the first and the second spatial end-points, respectively.

For some applications:
the flow regulator is configured to assume a third, intermediate fluid-control state, between the first and the second fluid-control states, in which (a) the suction source and the distal suction orifices are in fluid communication with one another, and (b) the interior of the inflation chamber and the interior of the inflatable element are not in fluid communication with one another, and
the flow regulator is configured to assume the third, intermediate fluid-control state when the mechanical user control element is in a third, intermediate configuration between the first configuration and the second configuration.

For some applications, the inflation module includes a one-way air inlet valve, which is arranged to allow air to flow into the inflation chamber during at least a portion of a transition of the mechanical user control element from the second configuration to the first configuration. For some applications, the one-way air inlet valve is configured to generate a sound signal during at least a portion of a period of fluid flow into the inflation chamber.

For any of the applications described hereinabove, the mechanical user control element may be configured to increase the pressure in the interior of the inflation chamber by mechanically and non-electrically compressing the inflation chamber during the at least a portion of the transition of the mechanical user control element from the first configuration to the second configuration.

For some applications, the inflation chamber transitions from a lower level of compression to a higher level of compression during the at least a portion of the transition of the mechanical user control element from the first configuration to the second configuration, and the input module is configured to elastically bias the inflation chamber toward the lower level of compression.

For some applications, the inflation module is elastically biased toward the lower level of compression.

For some applications, at least one wall of the inflation chamber is elastically biased toward the lower level of compression.

For some applications, the at least one wall of the inflation chamber is accordion-shaped.

For some applications, the inflation module includes an elastic element that is arranged to bias the inflation chamber toward the lower level of compression, For some applications, the mechanical user control element is elastically biased toward the lower level of compression.

For any of the applications described hereinabove, the catheter main body may include a proximal-most input portion, which is disposed within and axially slidable with respect to the input module.

For some applications, the input module is arranged such that changes in configuration of the mechanical user control element cause corresponding changes in axial position of the input portion of the catheter main body with respect to the input module.

For some applications, the input module is arranged such that the input portion assumes first and second axial positions with respect to the input module, corresponding to the first and the second configurations of the mechanical user control element.

For any of the applications described hereinabove, the catheter main body may include a proximal-most input portion, which is disposed within and fixed with respect to the input module.

For some applications:
the mechanical user control element includes a user control handle,
the input module is arranged such that the user control handle is moveable with respect to the catheter main body in two opposite directions along a movement axis that forms a fixed angle of between 45 and 135 degrees with a central longitudinal axis of the proximal-most input portion of the catheter main body, and
the input module is arranged such that movement of the user control handle along the movement axis mechanically causes corresponding movement, along or alongside the movement axis, of a distal opening of the suction port, which selectively brings the distal end of the suction port into and out of fluid communication with the interior of the inflatable element and the distal suction orifices.

For some applications:
the inflation chamber is shaped so as to define an outlet, and
the input module is arranged such that movement of the user control handle along the movement axis mechanically causes corresponding movement of the outlet of the inflation chamber along or alongside the movement axis, which selectively brings the interior of the inflation chamber into and out of fluid communication with the interior of the inflatable element.

For any of the applications described hereinabove, the inflation chamber may be disposed within the mechanical user control element.

For some applications, the mechanical user control element includes a user control handle, and the inflation chamber is defined by one or more interior surfaces of the user control handle.

For some applications, the input module includes exactly one mechanical user control element configured (a) to mechanically and non-electrically set the fluid-control states of the flow regulator, (b) to assume the at least first and second configurations, and (c) to mechanically and non-electrically increase the pressure in the interior of the inflation chamber during the at least a portion of the transition of the mechanical user control element from the first configuration to the second configuration.

There is further provided, in accordance with an application of the present invention, apparatus for use with a tracheal ventilation tube and a suction source, the apparatus including:
(A) a cleaning catheter, which (a) is insertable into the ventilation tube, (b) is shaped so as to define one or more distal suction orifices, and (c) which includes:
 (i) an elongate, flexible, tubular catheter main body, which includes a proximal-most input portion; and
 (ii) an inflatable element, which is mounted to the catheter main body at a location within 3 cm of at least one of the one or more distal suction orifices; and
(B) an input module, which is fixed to the proximal-most input portion of the catheter main body of the cleaning catheter, and includes:
 (i) a flow regulator, which (a) is shaped so as to define a suction port coupleable in fluid communication with the suction source, and (b) is configured to assume at least first and second fluid-control states and
 (ii) a mechanical user control element, which includes a user control handle, and which is configured (a) to mechanically and non-electrically set the fluid-control states of the flow regulator, and (b) to assume at least first and second spatial positions,
wherein the input module is arranged such that:
 the user control handle is moveable with respect to the catheter main body, in two opposite directions along a movement axis that forms a fixed angle of between 45 and 135 degrees with a central longitudinal axis of the proximal-most input portion of the catheter main body, and
 movement of the user control handle along the movement axis mechanically causes corresponding movement, along or alongside the movement axis, of a distal end of the suction port, which selectively brings the distal end of the suction port into and out of fluid communication with an interior of the inflatable element and the distal suction orifices.

For some applications, the suction port is coupled in fluid communication with the suction source.

For some applications, the mechanical user control element is biased toward the first spatial positions.

For some applications, the inflatable element includes a balloon.

For any of the applications described hereinabove:
the input module may further include an inflation module, which includes an inflation chamber separate from the suction source, and
the mechanical user control element may be configured to mechanically and non-electrically increase pressure in an interior of the inflation chamber during at least a portion of a transition of the mechanical user control element from the first spatial position to the second spatial position.

For some applications, the inflation chamber is disposed within the mechanical user control element.

For some applications, the inflation chamber is defined by one or more interior surfaces of the user control handle.

For some applications:
the inflation chamber is shaped so as to define an outlet, and
the input module is arranged such that movement of the user control handle along the movement axis mechanically causes corresponding movement of the outlet of the inflation chamber along or alongside the movement axis, which selectively brings the interior of the inflation chamber into and out of fluid communication with the interior of the inflatable element.

For some applications, the input module is arranged such that:
when the mechanical user control element is in the first spatial position, the flow regulator is in the first fluid-control state, in which the flow regulator blocks fluid communication between the suction source and the distal suction orifices, and
when the mechanical user control element is in the second spatial position, the flow regulator is in the second fluid-control state, in which the flow regulator (A) connects the suction source and the distal suction orifices in fluid communication, and (B) connects the interior of the inflation chamber and an interior of the inflatable element in fluid communication to inflate the inflatable element.

For some applications:
the flow regulator is configured to assume a third, intermediate fluid-control state, between the first and the second fluid-control states, in which (a) the suction source and the distal suction orifices are in-fluid communication with one another, and (b) the interior of the inflation chamber and the interior of the inflatable element are not in fluid communication with one another, and
the flow regulator is configured to assume the third, intermediate fluid-control state when the mechanical user control element is in a third, intermediate spatial position between the first configuration and the second configuration.

For some applications, the input module is arranged such that:
when the mechanical user control element is in the first spatial position and the flow regulator is in the first fluid-control state, the flow regulator connects the suction source and the interior of the inflatable element in fluid communication to deflate the inflatable element, and when the mechanical user control element is in the second spatial position and the flow regulator is in the second fluid-control state, the flow regulator does not connect the suction source and the interior of the inflatable element in fluid communication.

For some applications, the inflation module includes a one-way air inlet valve, which is arranged to allow air to flow into the inflation chamber during at least a portion of a transition of the mechanical user control element from the second spatial position to the first spatial position.

For some applications, the one-way air inlet valve is configured to generate a sound signal during at least a portion of a period of fluid flow into the inflation chamber.

For some applications, the input module is arranged such that when the mechanical user control element is in the first spatial position and the flow regulator is in the first fluid-control state, the flow regulator connects the interior of the inflation chamber and the interior of the inflatable element in fluid communication to deflate the inflatable element.

For some applications, the mechanical user control element is configured to increase the pressure in the interior of the inflation chamber by mechanically and non-electrically compressing the inflation chamber during the at least a portion of the transition of the mechanical user control element from the first spatial position to the second spatial position.

For some applications, the inflation chamber transitions from a lower level of compression to a higher level of compression during the at least a portion of the transition of the mechanical user control element from the first spatial position to the second spatial position, and the input module is configured to elastically bias the inflation chamber toward the lower level of compression.

For some applications, the inflation module is elastically biased toward the lower level of compression.

For some applications, at least one wall of the inflation chamber is elastically biased toward the lower level of compression.

For some applications, the at least one wall of the inflation chamber is accordion-shaped.

For some applications, the inflation module includes an elastic element that is arranged to bias the inflation chamber toward the lower level of compression.

For some applications, the mechanical user control element is elastically biased toward the lower level of compression.

There is still further provided, in accordance with an application of the present invention, apparatus for use with a tracheal ventilation tube and a suction source, the apparatus including:

(A) a cleaning catheter, which (a) is insertable into the ventilation tube, (b) is shaped so as to define one or more distal suction orifices, and (c) which includes:
  (i) an elongate, flexible, tubular catheter main body; and
  (ii) an inflatable element, which is mounted to the catheter main body at a location within 3 cm of at least one of the one or more distal suction orifices; and (B) an input module, which is coupled to the cleaning catheter, and includes:
  (i) a flow regulator, which (a) is shaped so as to define a suction port coupleable in fluid communication with the suction source, and (b) is configured to assume at least first and second fluid-control states;
  (ii) an inflation module; which includes an inflation chamber separate from the suction source; and
  (iii) a mechanical user control element, within which the inflation chamber is disposed; and which is configured (a) to mechanically and non-electrically set the fluid-control states of the flow regulator, (b) to assume at least first and second configurations, and (c) to mechanically and non-electrically increase pressure in an interior of the inflation chamber during at least a portion of a transition of the mechanical user control element from the first configuration to the second configuration.

For some applications, the mechanical user control element includes a user control handle, and the inflation chamber is defined by one or more interior surfaces of the user control handle.

For some applications, the input module is arranged such that:
  when the mechanical user control element is in the first configuration, the flow regulator is in the first fluid-control state, in which the flow regulator blocks fluid communication between the suction source and the distal suction orifices, and
  when the mechanical user control element is in the second configuration, the flow regulator is in the second fluid-control state, in which the flow regulator (A) connects the suction source and the distal suction orifices in fluid communication, and (B) connects the interior of the inflation chamber and an interior of the inflatable element in fluid communication to inflate the inflatable element.

For some applications, the suction port is coupled in fluid communication with the suction source.

For any of the applications described hereinabove, the catheter main body may include a proximal-most input portion, which is disposed within and fixed with respect to the input module.

For some applications:
the mechanical user control element includes a user control handle,
the input module is arranged such that the user control handle is moveable with respect to the catheter main body in two opposite directions along a movement axis that forms a fixed angle of between 45 and 135 degrees with a central longitudinal axis of the proximal-most input portion of the catheter main body, and
the input module is arranged such that movement of the user control handle along the movement axis mechanically causes corresponding movement, along or alongside the movement axis, of a distal end of the suction port, which selectively brings the distal end of the suction port into and out of fluid communication with the interior of the inflatable element and the distal suction orifices.

For some applications:
the inflation chamber is shaped so as to define an outlet, and
the input module is arranged such that movement of the user control handle along the movement axis mechanically causes corresponding movement of the outlet of the inflation chamber along or alongside the movement axis, which selectively brings the interior of the inflation chamber into and out of fluid communication with the interior of the inflatable element.

There is additionally provided, in accordance with an application of the present invention, apparatus for use with a tracheal ventilation tube and a suction source, the apparatus including:
(A) a cleaning catheter, which (a) is insertable into the ventilation tube, (b) is shaped so as to define one or more distal suction orifices, and (c) which includes:
  (i) an elongate, flexible, tubular catheter main body; and
  (ii) an inflatable element, which is mounted to the catheter main body at a location within 3 cm of at least one of the one or more distal suction orifices; and
(B) an input module, which is coupled to the cleaning catheter, and includes:
  (i) an inflation module, which includes an inflation chamber separate from the suction source;
  (ii) a flow regulator, which (a) is shaped so as to define a suction port coupleable in fluid communication with the suction source, and (b) is configured to assume at least first and second fluid-control states;
  (iii) a first mechanical user control button, which is configured to (a) assume at least first and second configurations, and (h) mechanically and non-electrically set the fluid-control states of the flow regulator;
  (iv) a second mechanical user control button, which is configured to (a) to assume at least first and second configurations, and (b) mechanically and non-electrically increase pressure in an interior of the inflation chamber during a transition of the second mechanical user control button from its first configuration to its second configuration,
wherein the input module is arranged such that:
  at least when the first mechanical user control button is in its first configuration, the flow regulator is in the first fluid-control state, in which the flow regulator (a) blocks fluid communication between the suction source and the distal suction orifices and (b) connects the suction source and an interior of the inflatable element in fluid communication to deflate the inflatable element,
  at least when the first mechanical user control button is in its second configuration, the flow regulator is in the second fluid-control state, in which the flow regulator (a) connects the suction source and the distal suction orifices in fluid communication, and (b) connects the interior of the inflation chamber and an interior of the inflatable element in fluid communication to inflate the inflatable element, and
  the flow regulator is (a) not in the first fluid-control state when the first mechanical user control button is in its second configuration, and (b) not in the second fluid-control state when the first mechanical user control button is in its first configuration.

For some applications, the first and the second mechanical user control buttons are arranged such that a portion of one of the first and the second mechanical user control buttons at least partially surrounds the other of the first and the second mechanical user control buttons.

For some applications, the first and the second mechanical user control buttons are arranged such that a closest distance between the first and the second mechanical user control buttons is between 0.1 mm and 2 mm.

For some applications, the input module is configured such that during the at least a portion of the transition of the first mechanical user control button from its first configuration to its second configuration, before the flow regulator assumes the second fluid-control state, a volume of the interior of the inflation chamber decreases by between 10% and 90%.

For some applications, the second mechanical user control button is configured to mechanically and non-electrically increase the pressure in the interior of the inflation chamber during motion of the second mechanical user control button while the flow regulator is in the second fluid-control state.

For some applications, the suction port is coupled in fluid communication with the suction source.

For some applications, the input module further includes a user signal generator, which is configured to generate a user signal during or upon deflation of the inflatable element.

For some applications, the inflation chamber has a volume of between 1 and 10 cc when the mechanical user control element is in the first configuration.

For some applications, when the second mechanical user control button is in the second configuration, the inflation chamber has a volume of at least 1 cc less than when the second mechanical user control button is in the first configuration.

For some applications, the first mechanical user control button is biased toward its first configuration.

For some applications, the second mechanical user control button is biased toward its first configuration.

For some applications, the first and the second configurations of the first mechanical user control button are first and second spatial positions, respectively, and the first mechanical user control button is configured to assume at least the first and the second spatial positions.

For some applications, the first and the second configurations of the second mechanical user control button are first and second spatial positions, respectively, and the second mechanical user control button is configured to assume at least the first and the second spatial positions.

For some applications:
  the flow regulator is configured to assume a third, intermediate fluid-control state, between the first and the second fluid-control states, in which (a) the suction source and the distal suction orifices are in fluid communication with one another, and (b) the interior of the inflation chamber and the interior of the inflatable element are not in fluid communication with one another, and
  the flow regulator is configured to assume the third, intermediate fluid-control state when the first mechanical user control button is in a third, intermediate configuration between its first configuration and its second configuration.

For any of the applications described hereinabove, the inflation module may include a one-way air inlet valve, which is arranged to allow air to flow into the inflation chamber during at least a portion of a transition of the second mechanical user control button from its second configuration to its first configuration.

For some applications, the one-way air inlet valve is configured to generate a sound signal during at least a portion of a period of fluid flow into the inflation chamber.

For any of the applications described hereinabove, the second mechanical user control button may be configured to increase the pressure in the interior of the inflation chamber by mechanically and non-electrically compressing the inflation chamber during the at least a portion of the transition of the second mechanical user control button from its first configuration to its second configuration.

For some applications, the inflation chamber transitions from a lower level of compression to a higher level of compression during the at least a portion of the transition of the second mechanical user control button from its first configuration to its second configuration, and the input module is configured to elastically bias the inflation chamber toward the lower level of compression.

For some applications, the inflation module is elastically biased toward the lower level of compression.

For some applications, at least one wall of the inflation chamber is elastically biased toward the lower level of compression.

For some applications, the at least one wall of the inflation chamber is accordion-shaped.

For some applications, the inflation module includes an elastic element that is arranged to bias the inflation chamber toward the lower level of compression.

For some applications, the second mechanical user control button is elastically biased toward the lower level of compression.

There is further provided, in accordance with an application of the present invention, a method for use with a tracheal ventilation tube and a suction source, the method including:
- coupling, in fluid communication with the suction source, a suction port of a flow regulator of an input module that (a) is configured to assume at least first and second fluid-control states, and (b) includes (i) an inflation module, which includes an inflation chamber separate from the suction source, and (ii) a mechanical user control element, which is configured to mechanically and non-electrically set the fluid-control states of the flow regulator;
- setting the mechanical user control element in a first configuration, in which the flow regulator is in a first fluid-control state, in which the flow regulator blocks fluid communication between the suction source and one or more distal suction orifices defined by a cleaning catheter that (a) is coupled to the input module and (b) includes (i) an elongate, flexible, tubular catheter main body, and (ii) an inflatable element, which is mounted to the catheter main body at a location within 3 cm of at least one of the one or more distal suction orifices, wherein at least when the mechanical user control element is in the first configuration, the flow regulator is in the first fluid-control state, in which the flow regulator connects the suction source and an interior of the inflatable element in fluid communication to deflate the inflatable element;
- while the mechanical user control element is in the first configuration, inserting the cleaning catheter, in a proximal to distal direction, into the ventilation tube inserted in a trachea of a patient, and advancing the cleaning catheter until a distal end of the catheter main body is axially disposed in the ventilation tube at a location more distal than an axial mid-point of the ventilation tube; and
- while the cleaning catheter is thus disposed, transitioning the mechanical user control element from the first configuration to a second configuration, in which the flow regulator is in a second fluid-control state, in which the flow regulator (a) connects the suction source and the distal suction orifices in fluid communication, and (b) connects an interior of the inflation chamber and an interior of the inflatable element in fluid communication to inflate the inflatable element,
- wherein the mechanical user control element is configured to mechanically and non-electrically increase pressure in an interior of the inflation chamber during at least a portion of the transitioning of the mechanical user control element from the first configuration to the second configuration.

For some applications, the input module is configured such that during the at least a portion of the transition of the mechanical user control element from the first configuration to the second configuration; before the flow regulator assumes the second fluid-control state, a volume of the interior of the inflation chamber decreases by between 10% and 90%.

For some applications, the inflation chamber includes a one-way air inlet valve, which is arranged to allow air to flow into the inflation chamber during at least a portion of a transition of the mechanical user control element from the second configuration to the first configuration.

The present invention will be more fully understood from the following detailed description of embodiments thereof, taken together with the drawings, in which:

BRIEF DESCRIPTION OF THE DRAWINGS

FIG. 3 is a schematic illustration of a catheter main body of the closed suction cleaning system of FIGS. 1 and 2, in accordance with an application of the present invention;

FIGS. 5A-C are schematic cross-sectional illustrations of a portion of the closed suction cleaning system of FIG. 4 in the first fluid-control state, a second fluid-control state, and a third fluid-control state, respectively, in accordance with an application of the present invention;

DETAILED DESCRIPTION OF APPLICATIONS

Figure 1:
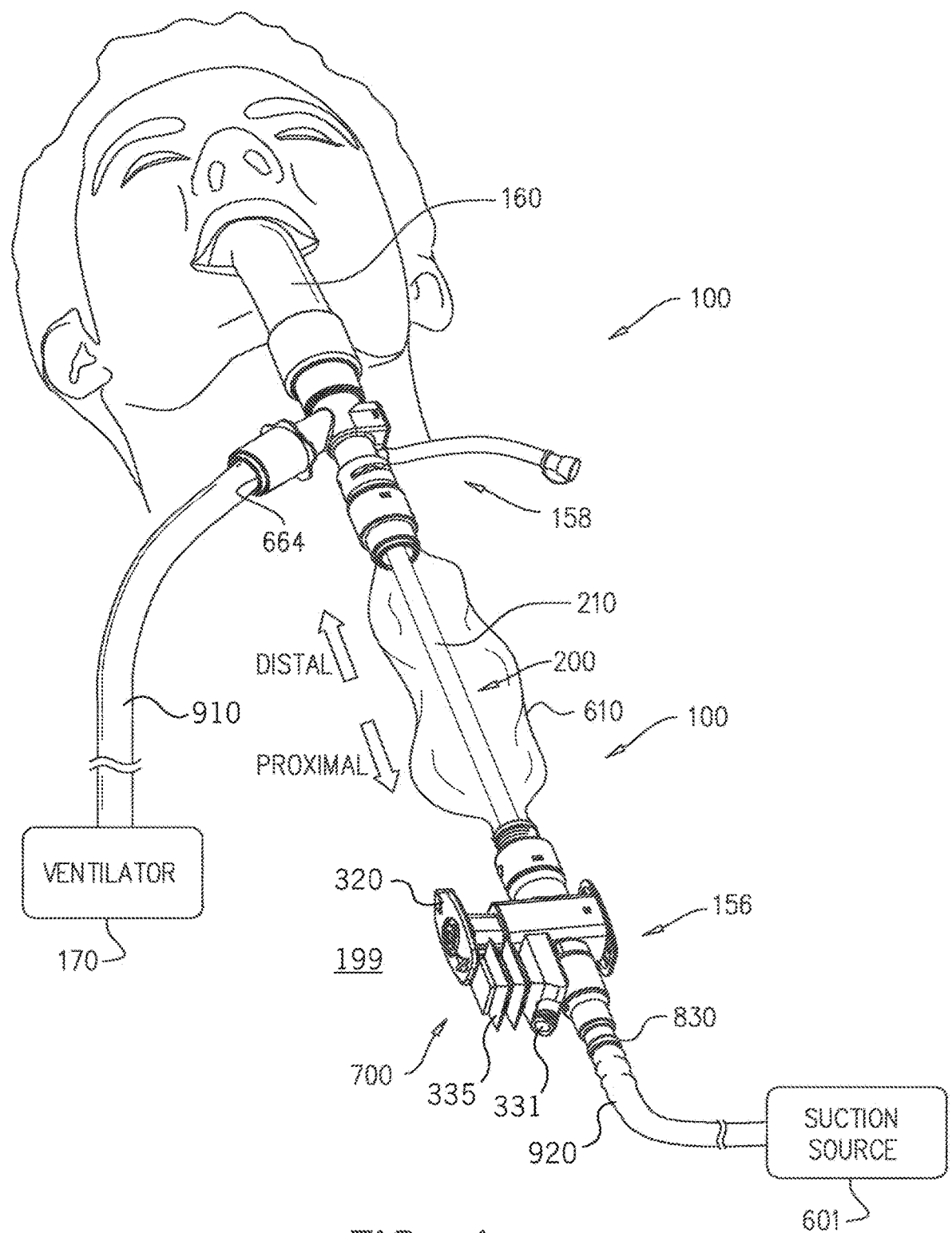
FIG. 1 is a schematic illustration of a closed suction cleaning system, in accordance with an application of the present invention.
Figure 2:
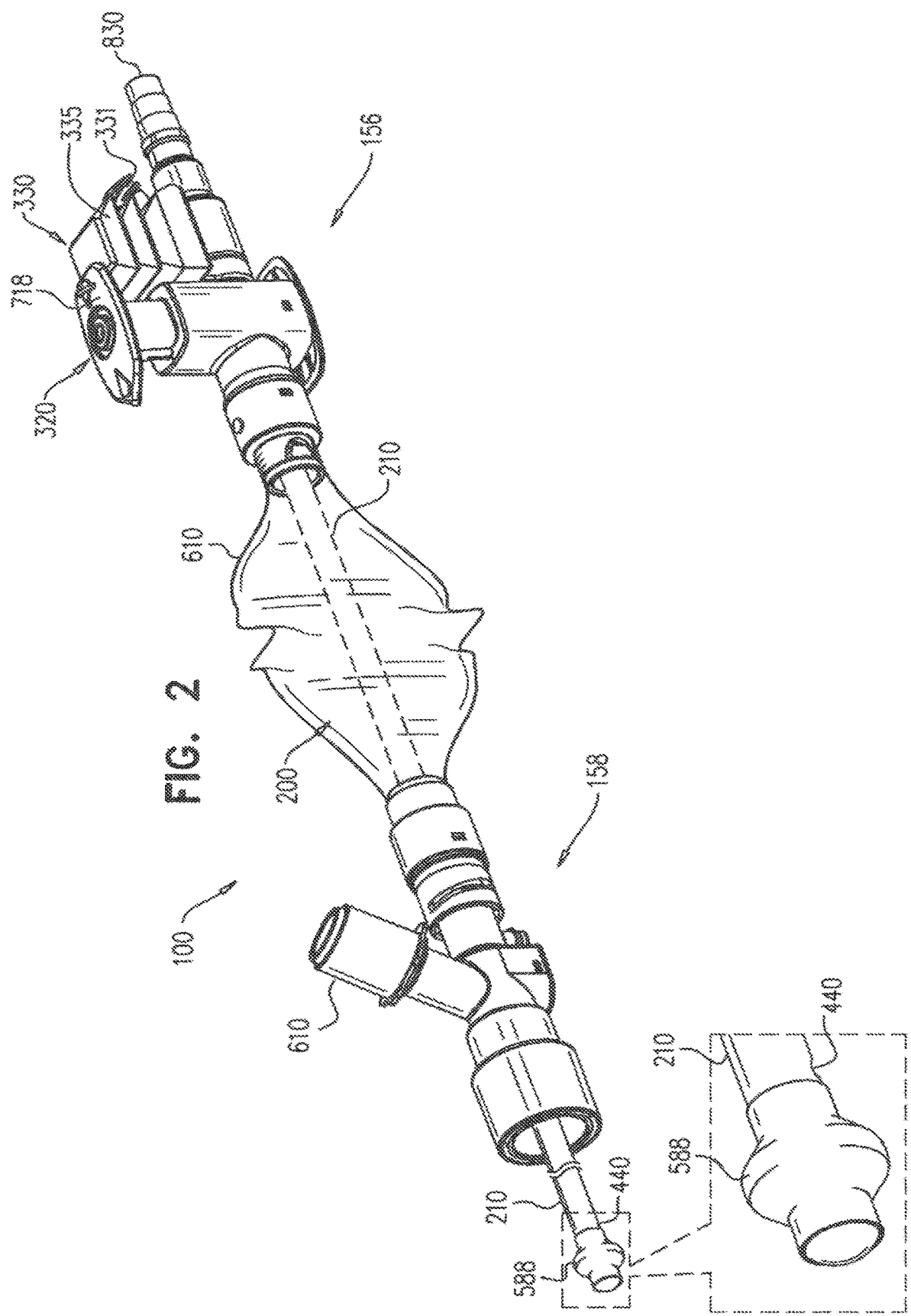
FIG. 2 is another schematic illustration of the closed suction cleaning system of FIG. 1, in accordance with an application of the present invention.

FIGS. 1 and 2 are schematic illustrations of a closed suction cleaning system 100, in accordance with an application of the present invention. Cleaning system 100 is configured for use with a tracheal ventilation tube 160, a ventilator 170, and a suction source 601. For some applications, cleaning system 100 comprises one or more of tracheal ventilation tube 160, ventilator 170, and/or suction source 601, in any combination.

As used in the present application, including in the claims, a "tracheal ventilation tube" comprises an endotracheal tube (ETT) or a tracheostomy tube. Suction source 601 provides a pressure less than one atm. As used in the present application, including in the claims, a "fluid" comprises liquid and/or gas, for example, a liquid-gas mixture that is predominantly liquid, such as a liquid with gas bubbles. The liquid may comprise water, such as saline solution or a disinfectant solution.

Cleaning system 100 comprises a distal ventilation tube-connector assembly 158, a cleaning catheter 200, and an input module 156. Cleaning catheter 200 comprises an elongate, flexible, tubular catheter main body 210. As shown in FIG. 3, described hereinbelow, cleaning catheter 200 includes a distal portion 212 located distal to ventilation tube-connector assembly 158, and a proximal portion 214 located proximal to ventilation tube-connector assembly 158. Distal portion 212 is configured to be inserted into ventilation tube 160. Proximal portion 214 includes a proximal-most input portion 216 of catheter main body 210, which is configured to be inserted into or is disposed within input module 156. For some applications, proximal-most input portion 216 is axially slidable with respect to input module 156, while for other applications, the proximal-most input portion is fixed with respect to the input module. Respective lengths of distal and proximal portions 212 and 214 may depend on an extent to which a distal end of catheter main body 210 is deployed within ventilation tube 160 and/or an extent to which the distal end is longitudinally displaced from ventilation tube-connector assembly 158, for example, an extent to which catheter main body 210 slides through ventilation tube-connector assembly 158 in a distal direction.

As used in the present application, including in the claims, "axial" and "axially" mean along an axis, and do not mean around or about an axis. For example: (a) "axial motion" means motion along an axis, and (b) "axially aligned" means aligned along an axis.

Ventilation tube-connector assembly 158 comprises: (a) a ventilator port 664, configured to be coupled in fluid communication with ventilator 170 via a ventilator connection tube 910, (b) a ventilation tube port, configured to be coupled in fluid communication with a proximal end of ventilation tube 160, and (c) a main body inlet, which is configured to allow passage therethrough of catheter main body 210.

In some applications of the present, invention, cleaning system 100 is operative to clean an interior of ventilation tube 160 when ventilation tube-connector assembly 158 is directly or indirectly connected to both ventilation tube 160 and ventilator 170 so as to mediate a substantially air-tight connection (e.g., via an interior chamber(s) and/or conduit(s) of ventilation tube-connector assembly 158) between the ventilator and an interior of the ventilation tube.

Cleaning catheter 200 further comprises an inflatable element 588, such as a balloon, which is mounted to catheter main body 210 near a distal end of catheter main body 210, e.g., within 3 cm, such as within 1 cm, of the distal end, and/or in a distal half of distal portion 212 of cleaning catheter 200, such as a distal third, a distal fifth, or a distal tenth of distal portion 212. Alternatively or additionally, inflatable element 588 is mounted to catheter main body 210 within 3 cm, e.g., within 1 cm, of at least one of the one or more distal suction orifices 440, described hereinbelow. Inflatable element 588 is inflatable into contact with an inner surface of ventilation tube 160. For some applications, inflatable element 588 has a greatest outer diameter of at least 6 mm, no more than 12 mm, and/or between 6 and 12 mm when inflated at 1 bar above atmospheric pressure and unconstrained (i.e., not constrained by the ventilation tube or anything else), which is typically slightly greater than an inner diameter of ventilation tube 160, in order to provide sealing contact with the inner surface of the ventilation tube. For some applications, inflatable element 588 has a volume of at least 0.5 cc, no more than 2 cc, and/or between 0.5 and 2 cc when inflated at 1 bar above atmospheric pressure and unconstrained. For some applications, inflatable element 588 is elastic, while for other applications inflatable element 588 is not elastic. For some applications, inflatable element 588 comprises a thin pliable material, such that the inflatable element crumples when deflated.

For some applications, catheter main body 210 has an outer diameter of at least 6 mm, no more than 12 mm, and/or between 6 and 12 mm. For some applications, the greatest outer diameter of inflatable element 588 when fully inflated and unconstrained (i.e., not constrained by the ventilation tube or anything else) equals at least 60%, no more than 120%, and/or between 60% and 120% of the outer diameter of catheter main body 210.

Reference is now made to FIG. 3, which is a schematic illustration of catheter main body 210, in accordance with an application of the present invention. Catheter main body 210 includes at least the following lumens arranged along catheter main body 210. For some applications, one or more of the lumens are arranged along catheter main body 210 at least partially within the main body, e.g., integrally formed in the catheter main body 210, formed in the wall of catheter main body 210, or provided as a separate tube with catheter main body 210. Alternatively or additionally, one or more of the lumens are arranged along catheter main body 210 at least partially outside the main body, e.g., provided as a separate tube outside catheter main body 210. The lumens include:

- at least one inflation lumen 520, which provides fluid communication between at least one inflation inlet 521 and at least one inflation port 585 which is in fluid communication with an interior of inflatable element 588; typically, input portion 216 is shaped so as to define inflation inlet 521, and distal portion 212 is shaped so as to define inflation port 585; and
- one or more suction lumens 530, which provide fluid communication between at least one proximal suction inlet 531 and the one or more distal suction orifices 440; typically, input portion 216 of catheter main body 210 is shaped so as to define proximal suction inlet 531, and distal portion 212 of cleaning catheter 200 is shaped so as to define distal suction orifices 440. The one or more suction lumens 530 are arranged in intermittent fluid communication with suction source 601, as described in detail hereinbelow; for applications in which the one or more suction lumens 530 comprise a plurality of suction lumens 530, the one or more suction lumens 530 typically are arranged in fluid communication with one another (and are thus typically brought into fluid communication with suction source 601 together rather than separately).

Inflation lumen 520 typically has a cross-sectional area smaller than that of suction lumen 530, e.g., less than 50%, less than 30%, or less than 20% of the cross-sectional area of suction lumen 530.

Reference is still made to FIG. 3, and is again made to FIGS. 1 and 2. When inflated, inflatable element 588 typically provides two types of functionality: (i) flow obstruction functionality to significantly hinder fluid flow between locations on opposite longitudinal sides of the inflatable element, and/or (ii) wiping functionality useful for cleaning the inner surface of ventilation tube 160. Typically, cleaning system 100 operates in a closed system environment.

During one state of operation, cleaning system 100 cleans the inner surface of ventilation tube 160 when ventilation tube-connector assembly 158 mediates a substantially air-tight seal between (i) ventilator 170 and/or an interior of ventilator port 664 and (ii) an interior of ventilation tube 160 and/or an interior of the ventilation tube port.

Concurrently with maintaining of this ventilation machine-ventilator tube seal, inflatable element 588 may be positioned within ventilation tube 160 (e.g., in a distal portion of ventilation tube 160), for example by moving a distal end of catheter main body 210 in a distal direction towards a distal end of ventilation tube 160. For example, inflatable element 588 may be distally advanced when inflatable element 588 is in a non-contact state (i.e., not in contact with the inner surface of ventilation tube 160). After inflatable element 588 is thus positioned, inflation of the inflatable element induces contact between an outer surface of inflatable element 588 and the inner surface of ventilation tube 160 and/or obstructs (i.e., significant hinders) longitudinal flow between proximal and distal portions of the interior of ventilation tube 160.

Upon inflation of inflatable element 588 when the inflatable element is positioned within ventilation tube 160, the inflated inflatable element forms a sliding boundary which obstructs (i.e., significantly hinders) fluid flow to between: (a) a more proximal portion of an interstitial region outside of catheter main body 210 and within ventilation tube 160 and (b) locations within the ventilation tube 160 that are distal to the slidable boundary formed and delineated by inflatable element 588. This slidable boundary between the proximal and distal portions may be useful for facilitating the cleaning of the inner surface of ventilation tube 160 (by wiping), for example for substantially confining locations of negative pressure and/or fluid (e.g., pressurized fluid) introduced into an interstitial region outside of catheter main body 210 and within ventilation tube 160 so that the suction is introduced predominantly in the proximal portion of ventilation tube 160.

Distal portion 212 of cleaning catheter 200 (labeled in FIG. 3) is shaped so as to define one or more distal suction orifices 440, typically through a lateral wall of distal portion 212. Typically, the one or more distal suction orifices 440 are located along distal portion 212 at one or more respective locations proximal to inflatable element 588. Typically, at least one of distal suction orifices 440 (such as all of the one or more distal suction orifices 440) is located within 1 cm of inflatable element 588, such as within 0.8 cm, e.g., within 0.5 cm of the inflatable element. For some applications, distal suction orifices 440 have a total cross-sectional area in aggregate of at least 2 mm2, no more than 25 mm2, and/or between 2 and 25 mm2, such as at least 4 mm2, no more than 16 mm2, and/or between 4 and 16 mm2.

Distal suction orifices 440 are supplied with negative pressure by suction source 601 and facilitate cleaning of the inner surface of ventilation tube 160. For some applications, material within the interior of ventilation tube 160 may be suctioned into distal suction orifices 440 and proximally transported out of ventilation tube 160, e.g., to a location that is proximal to ventilation tube-connector assembly 158. As described below in detail, fluid communication between suction source 601 and distal suction orifices 440 may be provided by one or more connecting lumens within or along catheter main body 210. As used in the present application, including in the claims, "fluid communication" includes both positive and negative pressure fluid communication, and thus includes, for example, communication of a positive pressure or of a suction force.

For some applications, cleaning system 100 comprises a substantially impermeable and/or pliable sleeve 610 for protecting an outer surface of catheter main body 210. In some embodiments, sleeve 610 envelops, surrounds, and/or protects at least some (e.g., at least a majority or at least a substantial majority, e.g., at least 75% or substantially all of (e.g., at least 90%)) of an outer surface of a ventilation-tube-connector-assembly-proximal portion 214 of catheter main body 210, typically in locations proximal to tube-connector assembly 158 and distal to suction port 830 (described hereinbelow), and typically to inhibit contamination. For some applications, sleeve 610 provides this enveloping and/or protection functionality when a length of the ventilation-tube-connector-assembly-proximal portion 214 (labeled in FIG. 3) of catheter main body 210 is at least 5 cm, e.g., at least 10 cm, at least 15 cm, or at least 20 cm.

For some applications, a length of proximal portion 214 may be modified by sliding, in a proximal or distal direction, catheter main body 210 through ventilation tube-connector assembly 158.

For some applications, a distal end of sleeve 610 is (i) directly or indirectly attached to and/or (ii) has a location that is fixed and/or longitudinally fixed relative to ventilation tube-connector assembly 158. For some applications, a longitudinal position of a location of the distal end of sleeve 610 corresponds to a location on ventilation tube-connector assembly 158 (e.g., at or near the main body inlet) and/or is longitudinally displaced from a proximal end (e.g., corresponding to the main body inlet) of ventilation tube-connector assembly 158 by at most 5 cm, e.g., at most 3 cm, at most 2 cm, or at most 1 cm, and/or at most 50%, e.g., at most 30%, at most 20%, at most 10% of a length of ventilation-tube-connector-assembly-proximal portion 214 of catheter main body 210.

For some applications, a location of the distal end of sleeve 610 is not fixed relative to catheter main body 210. For example, catheter main body 210 may be longitudinally slidable within the sleeve 610 at or near a location of the distal end. Alternatively or additionally, for some applications, a location of a proximal end of sleeve 610 is fixed and/or longitudinally fixed relative to a proximal end of catheter main body 210. For some applications, sleeve 610 forms a substantially air-tight seal between the external environment and an outer surface of ventilation-tube-connector-assembly-proximal portion 214 of catheter main body 210 and/or between the external environment and region of space outside of an outer surface of ventilation-tube-connector-assembly-proximal portion 214 of catheter main body 210 and within sleeve 610.

Figure 4:
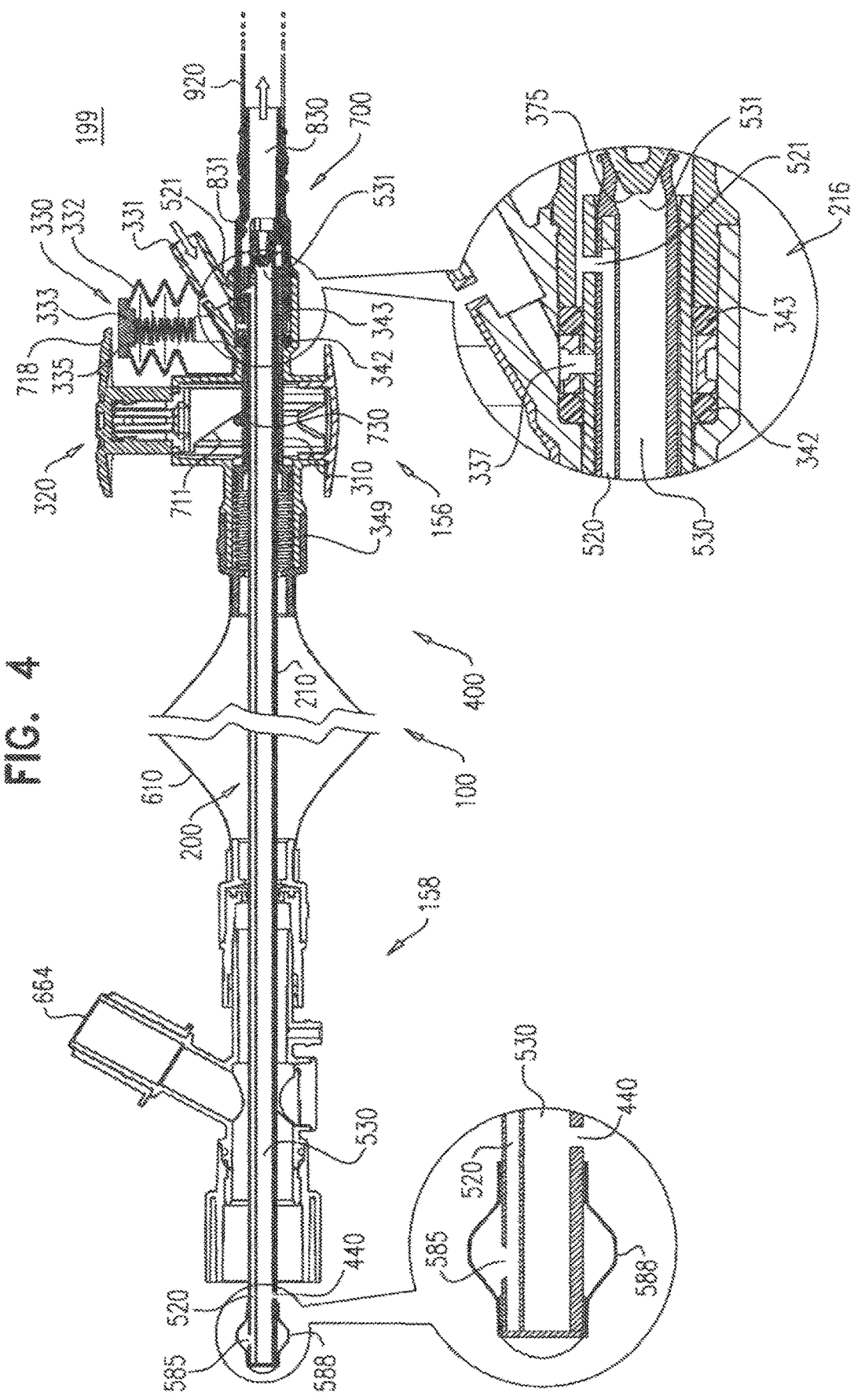
FIG. 4 is a schematic cross-sectional illustration of a closed suction cleaning system in a first fluid-control state, in accordance with an application of the present invention.

Reference is now made to FIG. 4, which is a schematic cross-sectional illustration of a closed suction cleaning system 400 in a first fluid-control state, in accordance with an application of the present invention. Reference is also made to FIGS. 5A-B, which are schematic cross-sectional illustrations of a portion of closed suction cleaning system 400 in the first fluid-control state and a second fluid-control state, respectively, in accordance with an application of the present invention. Closed suction cleaning system 400 is one implementation of closed suction cleaning system 100, described hereinabove with reference to FIGS. 1-3. For illustrative purposes, inflatable element 588 is shown inflated in FIGS. 4, even though the inflatable element is in practice not inflated in the first fluid-control state shown in FIG. 4, as described hereinbelow.

As mentioned above, in some configurations input portion 216 of proximal portion of catheter main body 210 is configured to be inserted into or is disposed within, and axially slidable with respect to, input module 156. Input module 156 has at least one port for connection with a fluid source, including at least suction source 601. Input module 156 is coupled to cleaning catheter 200, and comprises:

- an inflation module 330, which comprises an inflation chamber 335 separate from suction source 601;
- a flow regulator 700, which is (a) shaped so as to define suction port 830, which is coupleable in fluid communication with suction source 601 via a suction connection tube 920, and coupled in fluid communication with suction source 601 during use of cleaning system 100, and (b) configured to assume at least first and second fluid-control states;
- a mechanical user control element 320, which is configured (a) to mechanically and non-electrically set the fluid-control states of flow regulator 700, (b) to assume at least first and second configurations, and (c) to mechanically and non-electrically increase pressure in an interior of inflation chamber 335 during at least a portion of a transition of mechanical user control element 320 from the first configuration to the second configuration; and
- typically, a housing 310 encasing input portion 216 of catheter main body 210.

For some applications, the first and second configurations of mechanical user control element 320 are first and second spatial positions, respectively. Mechanical user control element 320 is configured to assume at least the first and the second spatial positions.

For some applications, input module 156 comprises exactly one mechanical user control element 320 having the properties described herein, and/or system 100 comprises exactly one mechanical user control element 320 having the properties described herein. Input module 156 and/or system 100 may comprise further user control elements that perform control functions in addition to those performed by mechanical user control element 320.

Input module 156 is arranged such that:

- at least when mechanical user control element 320 is in the first configuration (e.g., spatial position), as shown in FIGS. 2, 4, and 5A, flow regulator 700 is in the first fluid-control state, in which flow regulator 700 blocks fluid communication between suction source 601 and distal suction orifices 440,
- at least when mechanical user control element 320 is in the second configuration (e.g., spatial position), as shown in FIG. 5B, flow regulator 700 is in the second fluid-control state, in which flow regulator 700 (A) connects suction source 601 and distal suction orifices 440 in fluid communication, and (B) connects the interior of inflation chamber 335 and an interior of inflatable element 588 in fluid communication to inflate inflatable element 588, and
- flow regulator 700 is (a) not in the first fluid-control state when mechanical user control element 320 is in the second configuration, and (b) not in the second fluid-control state when mechanical user control element 320 is in the first configuration.

Typically, mechanical user control element 320 is able to assume an infinite number of intermediate configurations (e.g., spatial positions) between the first configuration and the second configuration, as mechanical user control element 320 transitions between the first configuration and the second configuration and vice versa. For some applications, mechanical user control element 320 is arranged to move between first and second spatial end-points, and the first and the second spatial positions correspond with the first and the second spatial end-points, respectively, as shown. Alternatively, the first and the second spatial positions do not correspond with the first and the second spatial end-points, respectively (configuration not shown), but instead the first spatial position and/or the second spatial position are between the first and the second spatial end-points. For some applications, the above-mentioned intermediate configurations include the third intermediate configuration (e.g., spatial position) described hereinbelow with reference to FIG. 5C.

Figure 5C:
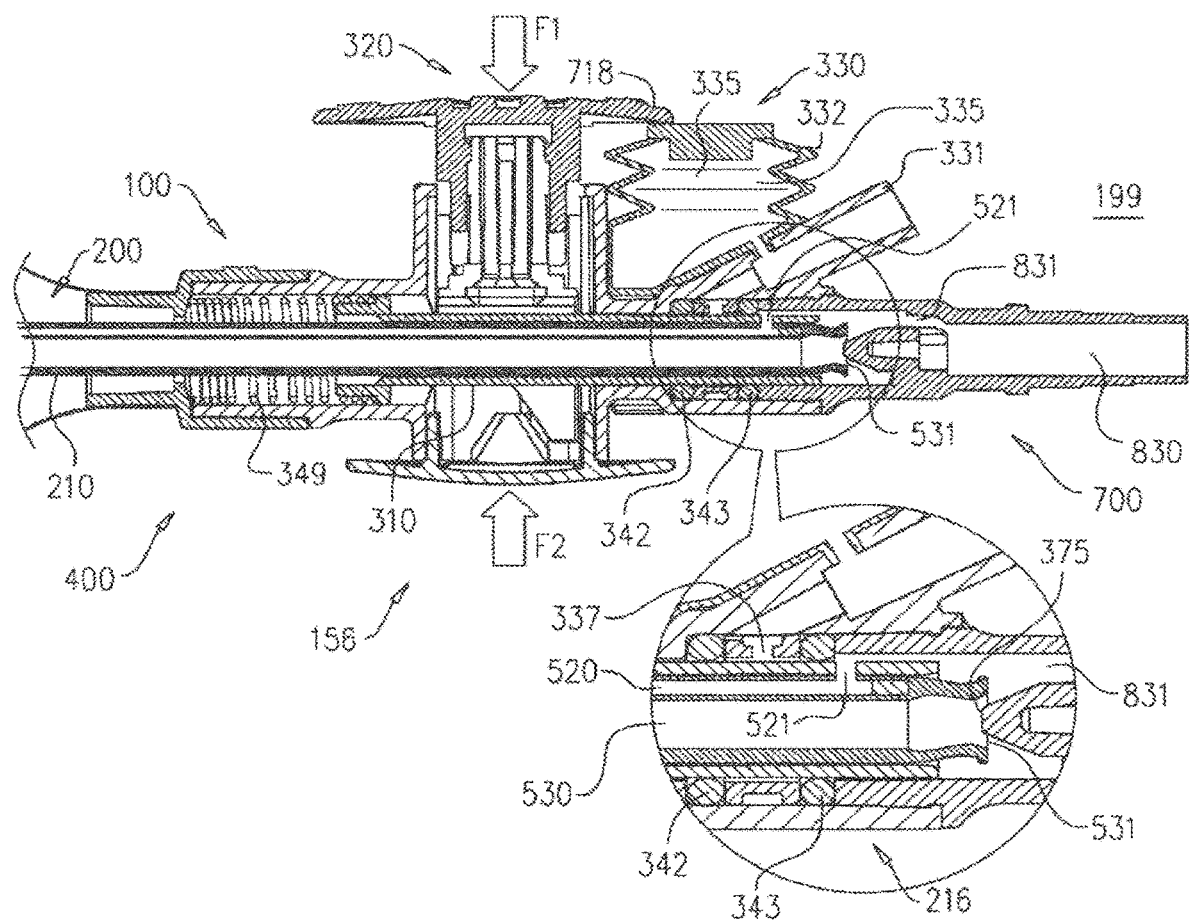

Input module 156 is typically arranged such that flow regulator 700 is in the first fluid-control state not only when mechanical user control element 320 is in the first configuration spatial position), as shown in FIGS. 2, 4, and 5A, but also during a portion of the intermediate configurations (e.g., spatial positions), which are typically contiguous with the first configuration (e.g., spatial position). Similarly, input module 156 is typically arranged such that flow regulator 700 is in the second fluid-control state not only when mechanical user control element 320 is in the second configuration (e.g., spatial position), as shown in FIG. 5B, but also during a portion of the intermediate configurations (e.g., spatial positions), which are typically contiguous with the second configuration (e.g., spatial position). For applications in which the intermediate configurations include the third, intermediate configuration (e.g., spatial position) described hereinbelow with reference to FIG. 5C, input module 156 is typically arranged such that flow regulator 700 is in the third fluid-control state not only when mechanical user control element 320 is in the third configuration (e.g., spatial position), as shown in FIG. 5C, but also during a portion of the intermediate configurations (e.g., spatial positions), which are typically contiguous with the third configuration (e.g., spatial position).

As mentioned above, mechanical user control element 320 is configured to mechanically and non-electrically increase pressure in an interior of inflation chamber 335 during at least a portion of the transition of mechanical user control element 320 from the first configuration to the second configuration. For some applications, mechanical user control element 320 is configured to mechanically and non-electrically increase the pressure in the interior of inflation chamber 335 during an entirety of the transition of mechanical user control element 320 from the first configuration to the second configuration.

For some applications, input module 156 is configured such that during the at least a portion of the transition of mechanical user control element 320 from the first configuration to the second configuration, before flow regulator 700 assumes the second fluid-control state, a volume of the interior of inflation chamber 335 decreases by at least 10%, such as at least 20%, 30%, 40%, or 50%, and/or no more than 90%, such as no more than 80% or 70%, e.g., by between 10% and 90%. In other words, the pressure in inflation chamber 335 increases substantially before fluid communication is established between the interior of inflation chamber 335 and the interior of inflatable element 588.

For some applications, the mechanical user control element 320 is configured to mechanically and non-electrically increase the pressure in the interior of inflation chamber 335 during motion of mechanical user control element 320 while flow regulator 700 is in the second fluid-control state. For example, the pressure may (a) continue to increase while flow regulator 700 is in the second fluid-control state, (b) increase only while flow regulator 700 is in the second fluid-control state, or (c) increase only while flow regulator 700 is in the second and the third fluid-control states.

As mentioned above, mechanical user control element 320 is configured to mechanically and non-electrically increase pressure in the interior of inflation chamber 335 during at least a portion of the transition of mechanical user control element 320 from the first configuration to the second configuration. For some applications, as labeled in FIG. 5B, a healthcare worker applies a first force F1 to mechanical user control element 320 (such as to a user control handle 718 thereof), and a second force F2, directed toward the first force F1, to the opposite side of input module 156 from mechanical user control element 320. Typically, mechanical user control element 320 is transitioned between the first and the second configurations when the distal end of catheter main body 210 is axially disposed in ventilation tube 160 at a location more distal than an axial mid-point of ventilation tube 160, typically near the distal end of ventilation tube 160 (typically within 2 cm of the distal end).

Typically, flow regulator 700:
  when in the first fluid-control state, connects suction source 601 and the interior of inflatable element 588 in fluid communication via an outlet 337 of inflation chamber 335 and inflation lumen 520, and
  when in the second fluid-control state, connects in fluid communication (a) suction source 601 and distal suction orifices 440 via the one or more suction lumens 530, and (b) the interior of inflation chamber 335 and the interior of inflatable element 588 via inflation lumen 520.

Optionally, seals 342 and 343 are provided to seal around outlet 337.

For some applications, such as shown in FIGS. 2, 3, 4, and 5A-B, input module 156 is arranged such that:
  when mechanical user control element 320 is in the first configuration (e.g., spatial position) and flow regulator 700 is in the first fluid-control state, as shown in FIGS. 2, 4 and 5A, flow regulator 700 connects suction source 601 and the interior of inflatable element 588 in fluid communication to deflate inflatable element 588, and
  when mechanical user control element 320 is in the second configuration (e.g., spatial position) and flow regulator 700 is in the second fluid-control state, as shown in FIG. 5B, flow regulator 700 does not connect suction source 601 and the interior of inflatable element 588 in fluid communication.

In these applications, typically flow regulator 700, when in the second fluid-control state, connects in fluid communication suction source 601 and distal suction orifices 440 via the one or more suction lumens 530.

Typically, each of the first and the second configurations of mechanical user control element 320 includes a range of spatial positions, such that each of the first and the second fluid-control states of flow regulator 700 is stably activated over the respective range of spatial positions, rather than only at single respective spatial positions of mechanical user control element 320. Providing these ranges of spatial positions obviates the need for the user to precisely position mechanical user control element 320 in order to achieve the different fluid-control states.

For some of these applications, inflation module 330 comprises a one-way air inlet valve 331, which is arranged to allow air to flow into inflation chamber 335 during at least a portion of a transition of mechanical user control element 320 from the second configuration to the first configuration. One-way air inlet valve 331 allows ambient air 199 to enter (be sucked into) inflation chamber 335 as inflation chamber 335 expands during at least a portion of a transition between the second fluid-control state to the first fluid-control state. For some applications, one-way air inlet valve 331 is configured to generate a sound signal during at least a portion of a period of fluid flow into inflation chamber 335 and/or during deflation of inflatable element 588; for example, one-way air inlet valve 331 may be shaped so as to define a whistle.

In the configuration illustrated in FIGS. 1-2, 4, 5A-C, 8-9, 10, and 11A-C the two fluid-control states are actuated by axial motion of proximal portion 214 of catheter main body 210 relative to input module housing 310. For some applications, transitions between the two states are caused by shifts in alignment of the lumen inlets with respect to various chambers of input module 156, which chambers are or are not in fluid communication with respective ports. The shifts in alignment are typically caused via axial motion of input portion 216 of catheter main body 210 within input module housing 310, along the longitudinal axes of input portion 216 and input module 156. For some applications, input module 156 is arranged such that changes in configuration of mechanical user control element 320 cause corresponding changes in axial position of input portion 216 with respect to input module 156. Typically, for these applications, input module 156 is arranged such that input portion 216 assumes first and second axial positions with respect to input module 156; corresponding to the first and the second configurations of mechanical user control element 320.

Typically, suction port 830 is shaped as a conventional suction port in accordance with hospital standards for coupling to standard hospital suctions sources. For example, suction port 830 may have a male conical interface, such as shown in FIGS. 2, 4, 5A-C, 8-9, 10, and 11A-C. Typically, suction port 830 has a lumen size that corresponds with the lumen size of conventional tracheal suction lumens, which generally having a gauge of between 5 Fr to 18 Fr.

Reference is now made to FIG. 5C, which is a schematic cross-sectional illustration of a portion of closed suction cleaning system 400 in a third fluid-control state, in accordance with an application of the present invention. For some applications, cleaning system 400 may also be used for suctioning the trachea outside of and distal to ventilation tube 160, typically when flow regulator 700 is in one of the following states:
  as shown in FIG. 5B, the second fluid-control state, in which suction source 601 and distal suction orifices 440 are in fluid communication (and inflatable element 588 is inflated), or
  as shown in FIG. 5C, a third, intermediate fluid-control state, between the first and the second fluid-control states, in which (a) suction source 601 and distal suction orifices 440 are in fluid communication with one another, and (b) the interior of inflation chamber 335 and the interior of inflatable element 588 are not in fluid communication with one another, and inflatable element 588 is thus not inflated.

For some applications, flow regulator 700 is configured to assume the third, intermediate fluid-control state when mechanical user control element 320 is in a third, intermediate configuration (e.g., spatial position), as shown in FIG. 5C, between the first configuration (e.g., spatial position), as shown in FIG. 5A, and the second configuration (e.g., spatial configuration), as shown in FIG. 5B.

For some applications, when mechanical user control element 320 is in the third, intermediate configuration and flow regulator 700 is in the third, intermediate fluid-control state:
  inflation inlet 521 is not in fluid communication with outlet 337 of inflation chamber 335; typically, inflation inlet 521 is in fluid communication with suction port 830, such as via at least one suction channel 831, to maintain inflatable element 588 deflated, as shown in FIG. 5C (alternatively, inflation inlet 521 is axially aligned with a wall of input module housing 310, e.g., slightly proximal to (i.e., to the right of, in FIG. 5B) the position of inflation inlet 521 shown in FIG. 5B (and thus slightly proximal to outlet 337), because catheter main body 210 is positioned slightly proximal to (i.e., to the right of, in FIG. 5B) the position shown in FIG. 5B), and
  as shown in FIG. 5C, proximal suction inlet 531 is in fluid communication with suction port 830, such as via at least one suction channel 831, e.g., with proximal suction inlet 531 disposed slightly proximal to (i.e., to the right of, in FIG. 5B) the position of proximal suction inlet 531 shown in FIG. 5B, but not so proximal (e.g., far to the right in FIG. 5B) as to form a seal with suction sealer 375.

Typically, as described above regarding the first and the second configurations of mechanical user control element 320, the third configuration of mechanical user control element 320 includes a range of spatial positions, such that the third fluid-control state of flow regulator 700 is stably activated over the range of spatial positions, rather than only at a single spatial position of mechanical user control element 320. Providing this range of spatial positions obviates the need for the user to precisely position mechanical user control element 320 in order to achieve the third fluid-control states.

As mentioned above, for some of these applications, when mechanical user control element 320 is in the third, intermediate configuration and flow regulator 700 is in the third, intermediate fluid-control state, inflation inlet 521 is in fluid communication with suction port 830, as shown in FIG. 5C. For others of these applications, when mechanical user control element 320 is in the third, intermediate configuration and flow regulator 700 is in the third, intermediate fluid-control state, inflation inlet 521 is not in fluid communication with suction port 830 (configuration not shown).

For some applications, during a transition of mechanical user control element 320 between the first configuration and the second configuration, mechanical user control element 320 assumes a transient position in which inflation inlet 521 is neither in fluid communication with suction port 830 nor in fluid communication with outlet 337 of inflation chamber 335. Typically, the transient position has a shorter range of spatial positions than do the first, the second, and the third configurations of mechanical user control element 320, as described above.

For some applications, the distal end of catheter main body 210 is closed (such as shown). In these applications, tracheal suction is typically performed by advancing catheter main body 210 far enough beyond the distal end of ventilation tube 160 such that at least one of the one or more distal suction orifices 440 is in fluid communication with the interior of the trachea distally beyond the end of ventilation tube 160. For other applications, catheter main body 210 is shaped so as to define, in addition to the one or more distal suction orifices 440, a distal-most suction orifice at a distal end of distal portion 212 of cleaning catheter 200, distal to inflatable element 588, for example such as described in above-mentioned U.S. Pat. No. 8,999,074, with reference to FIGS. 21A-B and 22A-C thereof.

For some applications, input module 156 is configured such that changes in configuration (e.g., spatial position) of mechanical user control element 320 cause corresponding changes in axial position of input portion 216 of catheter main body 210 with respect to input module 156. Typically, input module 156 is configured such that input portion 216 assumes first and second axial positions with respect to input module 156 (e.g., with respect to suction port 830), corresponding to the first and the second configurations (e.g., spatial positions) of mechanical user control element 320. The first and the second axial positions of input portion 216 are typically along a single axis.

For some applications, such as shown in FIGS. 2, 4, 5A-C, 6A-C, and 7, mechanical user control element 320 is configured to increase the pressure in the interior of inflation chamber 335 by mechanically and non-electrically compressing inflation chamber 335 during the at least a portion of the transition of mechanical user control element 320 from the first configuration to the second configuration. In these applications, inflation chamber 335 functions as a compression pump. For some applications, mechanical user control element 320 is directly or indirectly coupled to one or more external surfaces of inflation chamber 335. Alternatively, as shown in FIGS. 1-2, 4, 5A-C, and 8-9, mechanical user control element 320 and inflation chamber 335 are not directly coupled together, but are arranged such that activation (e.g., movement) of mechanical user control element 320 applies a force to inflation chamber 335. For example, mechanical user control element 320 and inflation module 330 (and inflation chamber 335) may be arranged such that user control handle 718 or a button of mechanical user control element 320 applies a force to a top surface of inflation module 330 (e.g., inflation chamber 335) when the handle or button is pressed toward an axis of input module 156. Alternatively, for example, inflation chamber 30 may be disposed at least partially within mechanical user control element 320 (such as described hereinbelow with reference to FIGS. 6A-C and 7). Other configurations will be readily apparent to one of ordinary skill in the art who has read the present application, and are within the scope of the present application.

For some applications, as shown in FIGS. 1-2, 4, 5A-C, 6A-C, 7, and 8-9, inflation chamber 335 transitions from a lower level of compression to a higher level of compression during the at least a portion of the transition of mechanical user control element 320 from the first configuration to the second configuration. For some of these applications, input module 156 is configured to elastically bias inflation chamber 335 toward the lower level of compression. For some applications, inflation chamber 335 (e.g., at least one wall 332 of inflation chamber 335) is elastically biased toward the lower level of compression. For example, the at least one wall of inflation chamber 335 may be accordion-shaped and/or the chamber walls comprise an elastic material, such as silicon, rubber, or polyurethane. In some embodiments, substantially no friction needs to be overcome during expansion of inflation chamber 335. Alternatively or additionally, inflation module 330 (such as inflation chamber 335) comprises a distinct elastic element 333 (e.g., a spring) that is arranged to bias inflation chamber 335 toward the lower level of compression. Alternatively or additionally, mechanical user control element 320 is elastically biased toward the lower level of compression (and to the first configuration), for example by a spring 349. In any event, typically, when user control element 320 is released, inflation chamber 335 expands. In other words, input module 156 is biased to assume the first configuration and first fluid-control state when in a resting state, such that inflation chamber 335 is in an expanded state when input module 156 is in the resting state.

For some applications, input module 156 further comprises a user signal generator, which is configured to generate a user signal (e.g., a sound) during at least a portion of a period of fluid flow into inflation chamber 335 and/or during or upon deflation of inflatable element 588. The user signal generator may be electrical and/or mechanical.

For some applications, inflation chamber 335 has a volume of at least 1 cc, no more than 10 cc, and/or between 1 and 10 cc (e.g., at least 1.5 cc, no more than 3 cc, and/or between 1.5 and 3 cc), when mechanical user control element 320 is in the first configuration (i.e., not compressed). The volume typically equals more than 1 times and less than 3 times the volume of inflatable element 588. Typically, when mechanical user control element 320 is in the second configuration (i.e., compressed), inflation chamber 335 has a volume of at least 1 cc less than when mechanical user control element 320 is in the first configuration (i.e., not compressed).

Reference is made to FIGS. 4 and 5A-C. For some applications, as shown in these figures, catheter main body 210 is shaped so as to define proximal suction inlet 531 at a proximal end of the main body. For some of these applications, proximal suction inlet 531 is configured to sealingly engage a suction sealer 375 that is fixed with respect to housing 310. When flow regulator 700 is in the first fluid-control state, proximal suction inlet 531 is sealingly engaged with suction sealer 375 (as shown in FIGS. 4 and 5A), thereby blocking (a) fluid communication between proximal suction inlet 531 and suction port 830, and (b) fluid communication between suction source 601 and lumen 530. When flow regulator 700 is in the second fluid-control state, proximal suction inlet 531 is disengaged from suction sealer 375 (as shown in FIG. 5B), thereby enabling fluid communication between proximal suction inlet 531 and suction port 830. This engaging/disengaging is typically actuated by axial motion of catheter main body 210 with respect to suction sealer 375.

Typically, as shown in FIG. 5B, at least one suction channel 831 facilitates fluid communication to suction port 830 around the suction sealer 375. Therefore, when inflation inlet 521 is in fluid communication with suction channel 831, suction is communicated to inflation lumen 520, while suction remains blocked by suction sealer 375 from communication to one or more suction lumens 530. As a result, suction deflation of inflatable element 588 is caused while no suction is communicated to distal suction orifices 440 of the catheter main body.

For some applications, as shown in FIGS. 1-2, 4, 5A-C, and 8-9, mechanical user control element 320 comprises user control handle 718, the movement of which includes a component perpendicular to the associated axial motion of catheter main body 210. Mechanical user control element 320 translates the movement of user control handle 718 into axial motion of catheter main body 210. For example, mechanical user control element 320 may comprise a side projection element 730 attached to catheter main body 210, and an engaging element 711 that has a diagonal face which engages side projection element 730, such that when engaging element 711 moves down, it pushes side projection element 730 sideways and thus imparts axial motion to catheter main body 210.

Figure 6A:
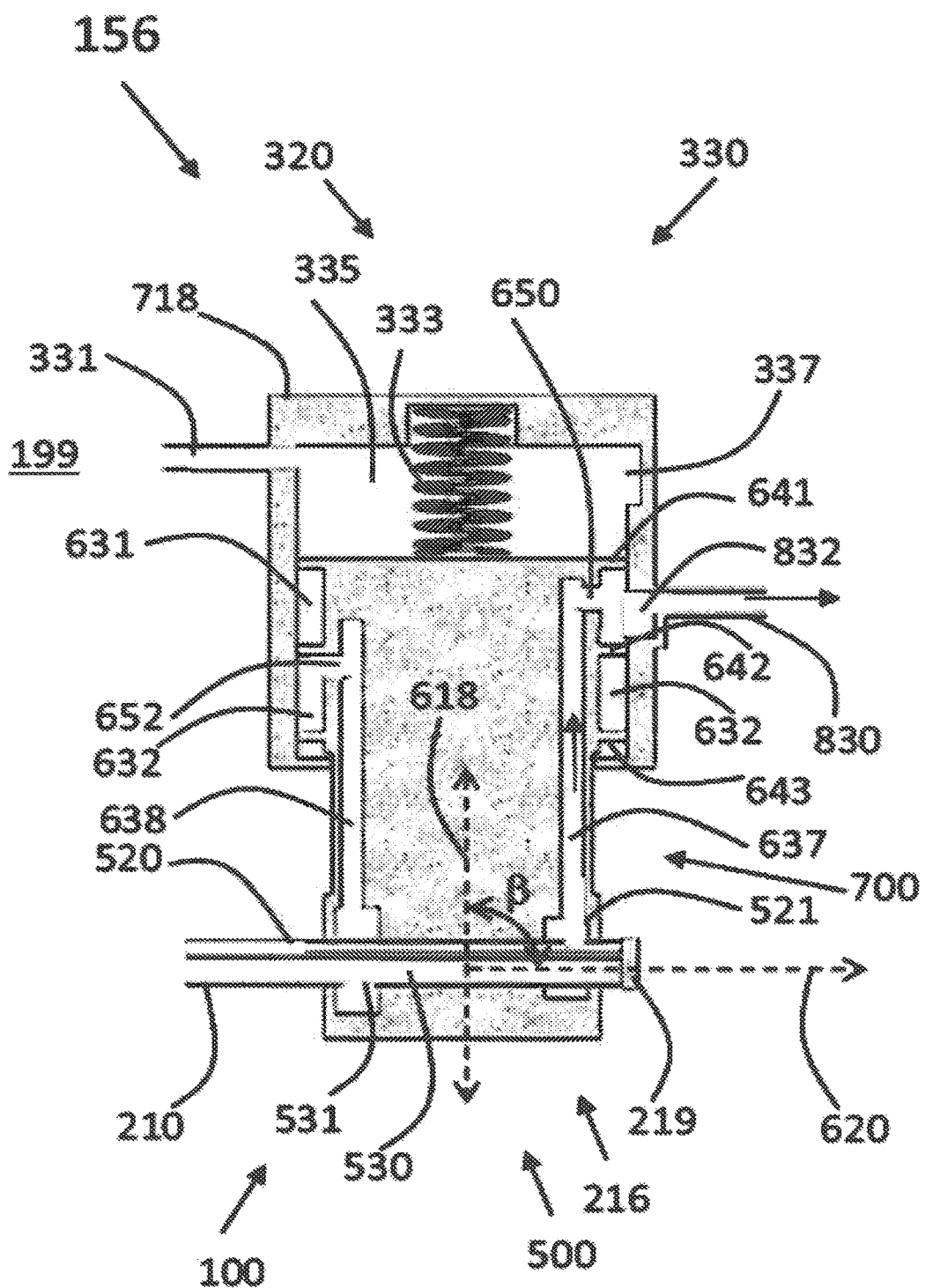
FIGS. 6A-C are schematic cross-sectional illustrations of another closed suction cleaning system in a first fluid-control state, a third intermediate fluid-control state, and a second fluid-control state, respectively, in accordance with an application of the present invention.
Figure 6B:
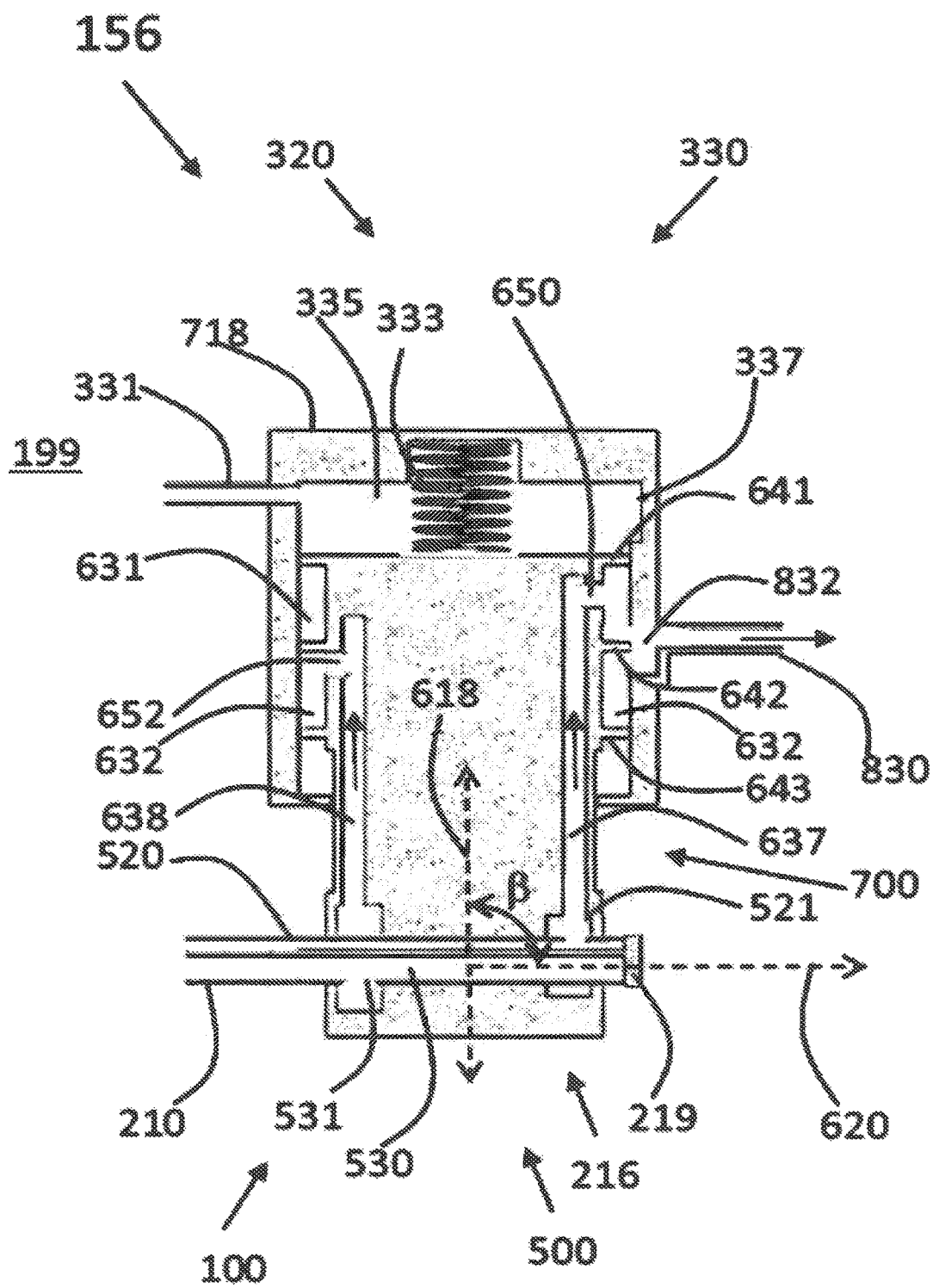
Figure 6C:
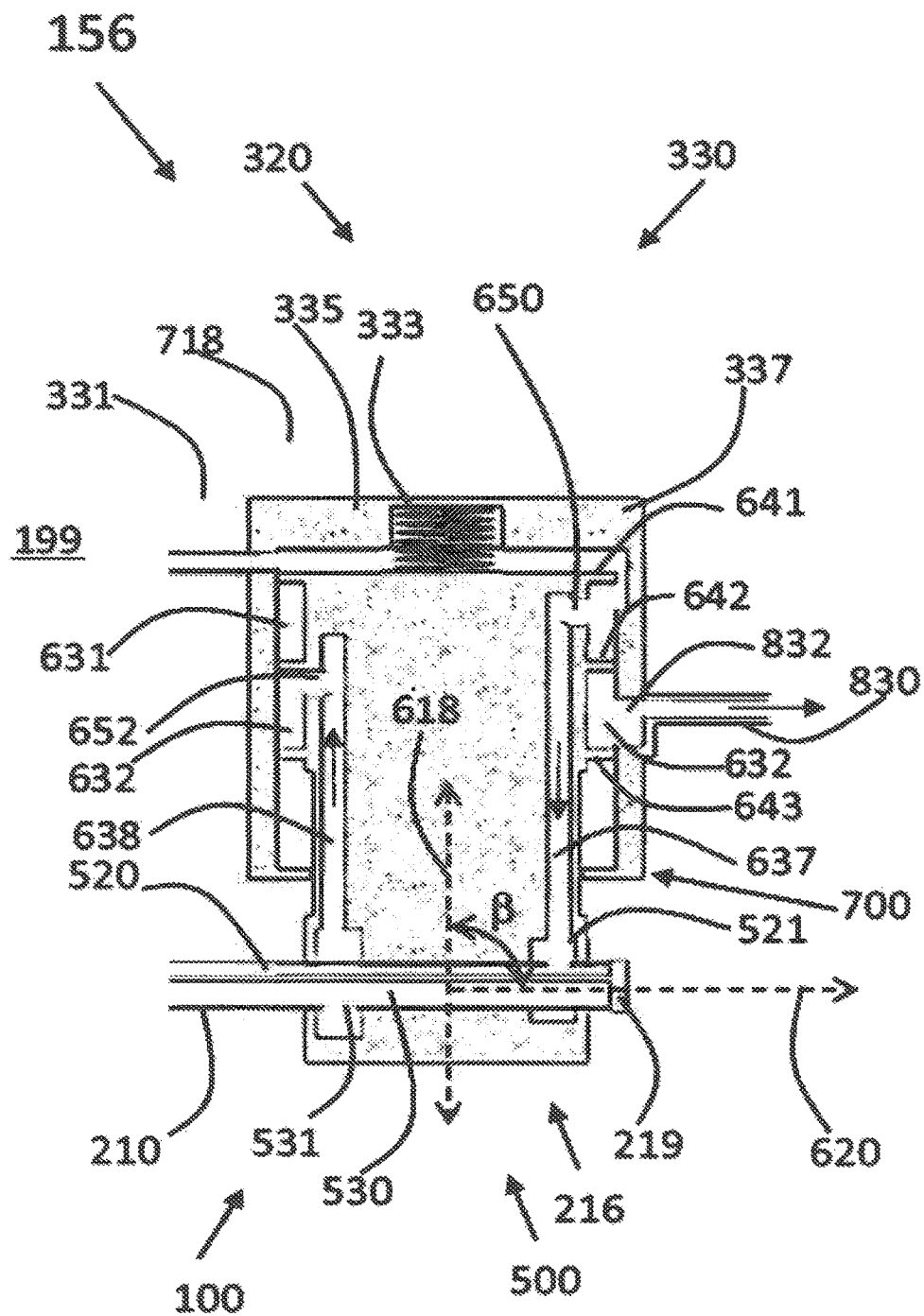
Figure 7:
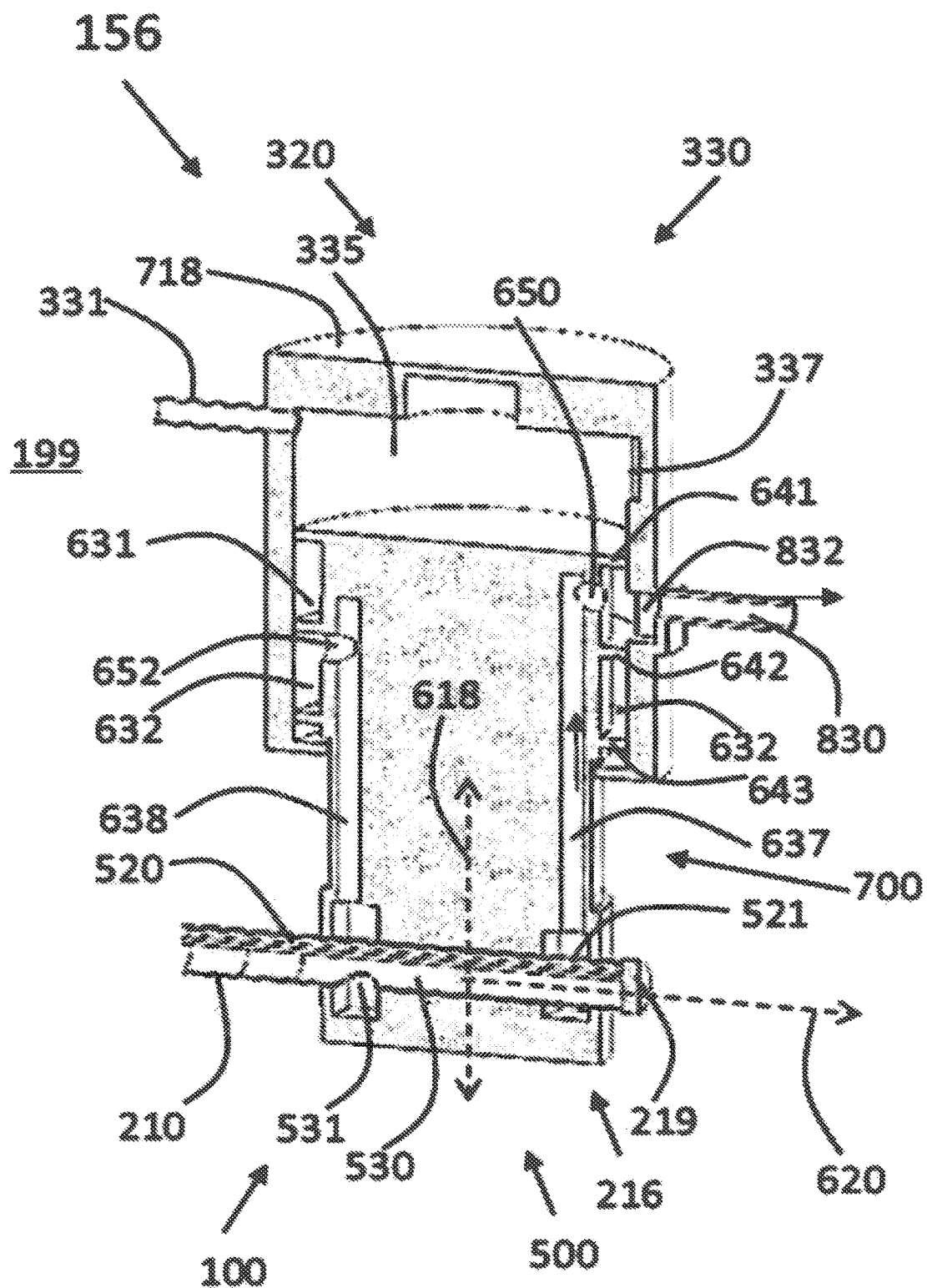
FIG. 7 is another schematic cross-sectional illustration of the closed suction cleaning system of FIGS. 6A-C in the First fluid-control state, in accordance with an application of the present invention.

Reference is now made to FIGS. 6A-C, which are schematic cross-sectional illustrations of a closed suction cleaning system 500 in a first fluid-control state, a third intermediate fluid-control state, and a second fluid-control state, respectively, in accordance with an application of the present invention. Reference is also made to FIG. 7, which is another schematic cross-sectional illustration of closed suction cleaning system 500 in the first fluid-control state, in accordance with an application of the present invention. Closed suction cleaning system 500 is one implementation of closed suction cleaning system 100, described hereinabove with reference to FIGS. 1-3, and, except as described hereinbelow, may implement any of the features described hereinabove with reference to FIGS. 1-3.

Unlike in the other configurations described herein, in closed suction cleaning system 500, the fluid-control states are not actuated by axial motion of proximal portion 214 of catheter main body 210 relative to input module housing 310, and mechanical user control element 320 does not translate the movement of user control handle 718 into axial motion of catheter main body 210. Instead, in closed suction cleaning system 500, proximal-most input portion 216 of catheter main body 210 is fixed with respect to input module 156. The movement of user control handle 718 actuates the fluid-control states without translating the movement into axial motion of proximal portion 214 of catheter main body 210. Input module 156 is arranged such that user control handle 718 is moveable with respect to catheter main body 210 in two opposite directions along a movement axis 618 that forms a fixed angle β (beta) of between 45 and 135 degrees with a central longitudinal axis 620 of proximal-most input portion 216 of catheter main body 210, typically 90 degrees (as shown). Input module 156 is arranged such that movement of user control handle 718 along movement axis 618 mechanically causes corresponding movement of a distal opening 832 of suction port 830 along or alongside movement axis 618. This corresponding movement selectively brings distal opening 832 of suction port 830 into and out of fluid communication with (a) the interior of inflatable element 588 (via inflation lumen 520 of catheter main body 210), and (b) distal suction orifices 440 (via suction lumen 530 of catheter main body 210), as described hereinbelow in detail. (Typically, input module 156 is arranged such that user control handle 718 is constrained to movement with respect to catheter main body 210 only along movement axis 618, and not in other directions.)

For some applications, module 156 is arranged such that movement of user control handle 718 along movement axis 618 mechanically causes corresponding movement of suction port 830 along or alongside movement axis 618, in addition to causing corresponding movement of distal opening 832 of suction port 830. For some of these applications, a longitudinal axis of suction port 830 is perpendicular to movement axis 618, and thus the longitudinal axis of suction port 830 moves along or alongside movement axis 618.

For some applications, mechanical user control element 320 is shaped so as to define first and second fluid-connection chambers 631 and 632, which are arranged at respective different locations along or alongside movement axis 618, with first fluid-connection chamber 631 farther from catheter main body 210 than second fluid-connection chamber 632 is from catheter main body 210. For some applications, first and second fluid-connection chambers 631 and 632 are annular (as shown). For example, in order to define the chambers, mechanical user control element 320 may be shaped so as to define, or comprise, first, second, and third sealing rings 641, 642, and 643 (e.g., O-rings), arranged such that first and second sealing rings 641 and 642 define first fluid-connection chamber 631, and second and third sealing rings 642 and 643 define second fluid-connection chamber 632.

For some applications, mechanical user control element 320 is shaped so as to define:
- an inflation lumen 637, which connects, in fluid communication, inflation inlet 521 of catheter main body 210 and first fluid-connection chamber 631, via an inflation lumen port 650 defined by inflation lumen 637, and
- a suction lumen 638, which connects, in fluid communication, proximal suction inlet 531 of catheter main body 210 and second fluid-connection chamber 632, via a suction lumen port 652 defined by suction lumen 638.

Inflation lumen port 650 may be disposed at or near an end of inflation lumen 637 opposite the end connected to inflation inlet 521 of catheter main body 210, as shown. Suction lumen port 652 may be disposed at or near an end of suction lumen 638 opposite the end connected to proximal suction inlet 531 of catheter main body 210, as shown.

Input module 156 is arranged such that when mechanical user control element 320 (e.g., user control handle 718 thereof) is in a first configuration (e.g., spatial position) along movement axis 618, as shown in FIGS. 6A and 7, flow regulator 700 is in the first fluid-control state, in which flow regulator 700:
- connects suction source 601 and the interior of inflatable element 588 in fluid communication via inflation lumen 520 to deflate inflatable element 588; for example, distal opening 832 of suction port 830 may be in fluid communication with first fluid-connection chamber 631, which in turn is in fluid communication with inflation inlet 521 via inflation lumen 637 and, and
- blocks fluid communication between suction source 601 and distal suction orifices 440 via suction lumen 530; for example, distal opening 832 of suction port 830 may not be in fluid communication with second fluid-connection chamber 632.

Input module 156 is arranged such that when mechanical user control element 320 is in the second configuration (e.g., spatial position) along movement axis 618, as shown in FIG. 6C, flow regulator 700 is in the second fluid-control state, in which flow regulator 700:
- connects suction source 601 and distal suction orifices 440 in fluid communication via suction lumen 530; for example, distal opening 832 of suction port 830 may be in fluid communication with second fluid-connection chamber 632, which in turn is in fluid communication with proximal suction inlet 531 via suction lumen 638, and
- connects the interior of inflation chamber 335 and the interior of inflatable element 588 in fluid communication to inflate inflatable element 588; for example, outlet 337 of inflation chamber 335 may be in fluid communication with first fluid-connection chamber 631, which in turn is in fluid communication with inflation inlet 521 via inflation lumen 637.

For some applications, input module 156 is arranged such that movement of user control handle 718 of mechanical user control element 320 along movement axis 618 mechanically causes corresponding movement along or alongside movement axis 618 of both:
- distal opening 832 of suction port 830, which selectively brings distal opening 832 of suction port 830 into and out of fluid communication with (a) the interior of inflatable element 588 (via inflation lumen 520 of catheter main body 210), and (b) distal suction orifices 440 (via suction lumen 530 of catheter main body 210), and
- outlet 337 of inflation chamber 335, which selectively brings the interior of inflation chamber 335 into and out of fluid communication with the interior of inflatable element 588 (via inflation lumen 520 of catheter main body 210).

For some applications, during movement of user control handle 718 of mechanical user control element 320 along movement axis 618, first and second fluid-connection chambers 631 and 632 remain stationary with respect to catheter main body 210 (as shown), while for other applications, first and second fluid-connection chambers 631 and 632 move with respect to catheter main body 210 (configuration not shown).

Reference is still made to FIGS. 6A-C and 7. For some applications, such as described hereinabove with reference to FIGS. 5A-C, cleaning system 100 may also be used for suctioning the trachea outside of and distal to ventilation tube 160, typically, when flow regulator 700 is in one of the following states:
- the second fluid-control state, in which suction source 601 and distal suction orifices 440 are in fluid communication (and inflatable element 588 is inflated), or
- the third, intermediate fluid-control state, between the first and the second fluid-control states, such as shown in FIG. 6B, in which (a) suction source 601 and distal suction orifices 440 are in fluid communication with one another, and (b) the interior of inflation chamber 335 and the interior of inflatable element 588 are not in fluid communication with one another, and inflatable element 588 is thus not inflated.

For some applications, flow regulator 700 is configured to assume the third, intermediate fluid-control state when mechanical user control element 320 is in a third, intermediate configuration (e.g., spatial position) along movement axis 618 between the first configuration (e.g., spatial position) and the second configuration (e.g., spatial configuration), such as shown in FIG. 6B.

For some applications, such as shown in FIG. 6B, when mechanical user control element 320 is in the third, intermediate configuration and flow regulator 700 is in the third, intermediate fluid-control state:
- inflation inlet 521 is not in fluid communication with outlet 337 of inflation chamber 335 (because outlet 337 is not in fluid communication with first fluid-connection chamber 631),
- proximal suction inlet 531 is in fluid communication with suction port 830, via suction lumen 638, second fluid-connection chamber 632, and distal opening 832 of suction port 830, and
- inflation inlet 521 is in fluid communication with suction port 830, via inflation lumen 637, first fluid-connection chamber 631, and distal opening 832 of suction port 830.

When flow regulator 700 is in the third, intermediate fluid-control state (shown in FIG. 6B), air pressure within inflation chamber 335 is greater than when flow regulator 700 is in the first fluid-control state (shown in FIG. 6A), because inflation chamber 335 has been compressed but the interior of the inflation chamber is not yet in fluid communication with any lumens, as the inflation chamber subsequently is in the second fluid-control state (shown in FIG. 6C).

When flow regulator 700 is in the third, intermediate fluid-control state, distal opening 832 of suction port 830 spans both first and second fluid-connection chambers 631 and 632 along or alongside movement axis 618 (because distal opening 832 of suction port 830 is wider than sealing ring 642, measured along or alongside movement axis 618). As a result, distal opening 832 of suction port 830 is simultaneously in fluid communication with both first and second fluid-connection chambers 631 and 632.

For some applications, as shown in FIGS. 6A-C and 7, inflation chamber 335 is disposed within mechanical user control element 320; for example, inflation chamber 335 may be defined by one or more interior surfaces of user control handle 718.

For some applications, inflation module 330 comprises a one-way air inlet valve 331, such as described hereinabove with reference to FIGS. 4 and 5A-C.

Figure 8:
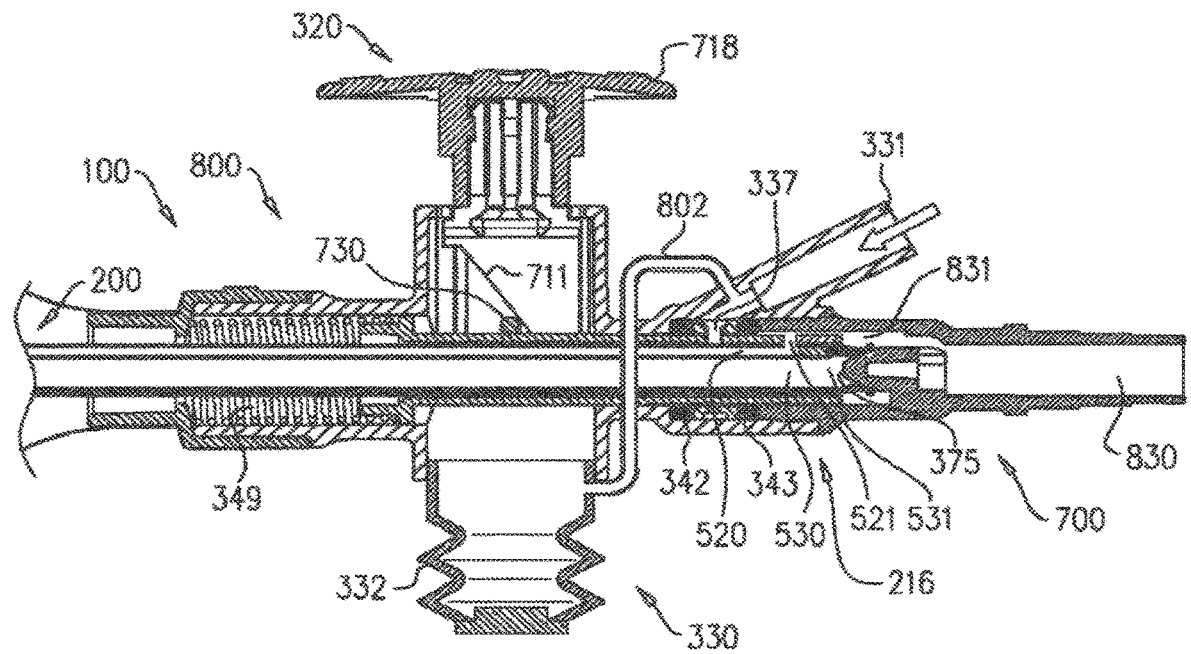
FIGS. 8 and 9 are schematic cross-sectional illustrations of yet another closed suction cleaning system in first and second fluid-control states, respectively, in accordance with an application of the present invention.
Figure 9:
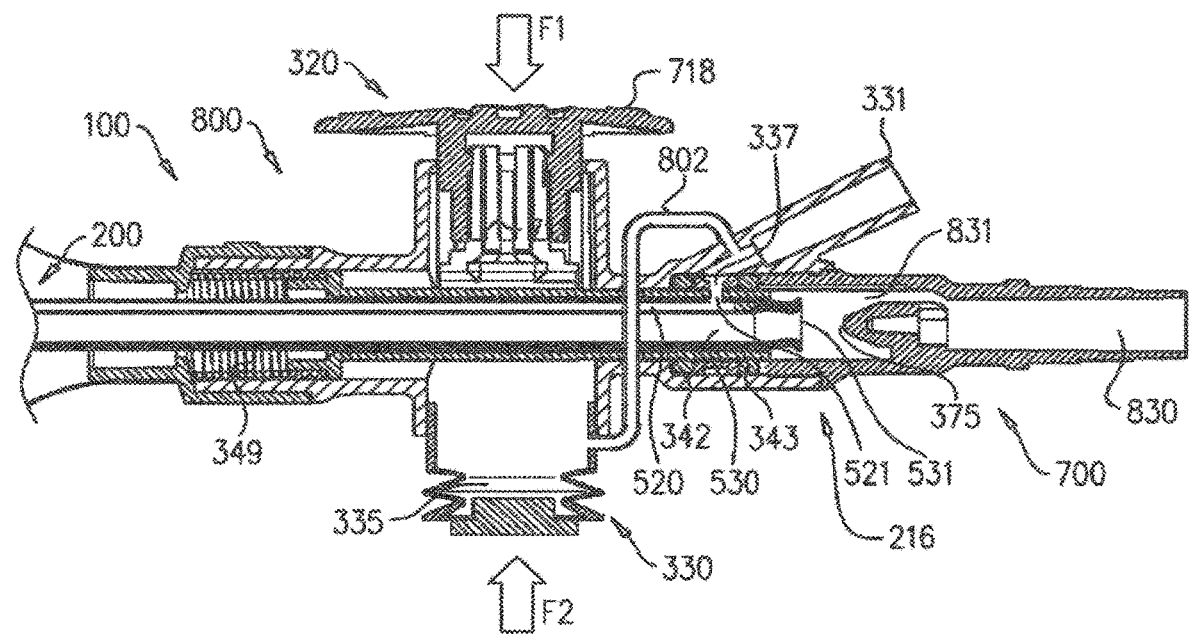

Reference is now made to FIGS. 8-9, which are schematic cross-sectional illustrations of a closed suction cleaning system 800 in first and second fluid-control states, respectively, in accordance with an application of the present invention. Closed suction cleaning system 800 is one implementation of closed suction cleaning system 100, described hereinabove with reference to FIGS. 1-3, and, except as described hereinbelow, may implement an of the features described hereinabove with reference to FIGS. 1-3. Although closed suction cleaning system 800 is shown in FIGS. 8-9 as implementing features of closed suction cleaning system 400, described hereinabove with reference to FIGS. 4 and 5A-C, closed suction cleaning system 800 may alternatively implement features of closed suction cleaning system 500, described hereinabove with reference to FIGS. 6A-C and 7, mutalis mutandis.

In closed suction cleaning system 800, inflation module 330 (including inflation chamber 335) is arranged on the opposite side of input module 156 from mechanical user control element 320. Outlet 337 of inflation module 330 may be connected to chamber 335 by a tube 802. Input module 156 is arranged such that flow regulator 700 assumes the first fluid-control state when in a resting state; to this end, mechanical user control element 320 is elastically biased toward the first configuration, for example by spring 349, and inflation chamber 335 is elastically biased toward the lower level of compression, for example as described hereinabove with reference to FIGS. 2, 4, 5A-C, 6A-C, and 7.

Simultaneous application of respective forces (labeled as first force F1 and second force F2), directed toward each other, to mechanical user control element 320 and inflation module 330 (and inflation chamber 335), simultaneously:
transitions mechanical user control element 320 from the first configuration to the second configuration, thereby transitioning flow regulator 700 from the first fluid-control state to the second fluid-control state, and
mechanically and non-electrically increases pressure in the interior of inflation chamber 335, by compression of inflation chamber 335.

The respective forces are typically applied by a healthcare worker squeezing mechanical user control element 320 and inflation module 330 (and inflation chamber 335) toward each other, such as using the thumb and fingers, respectively.

Figure 10:
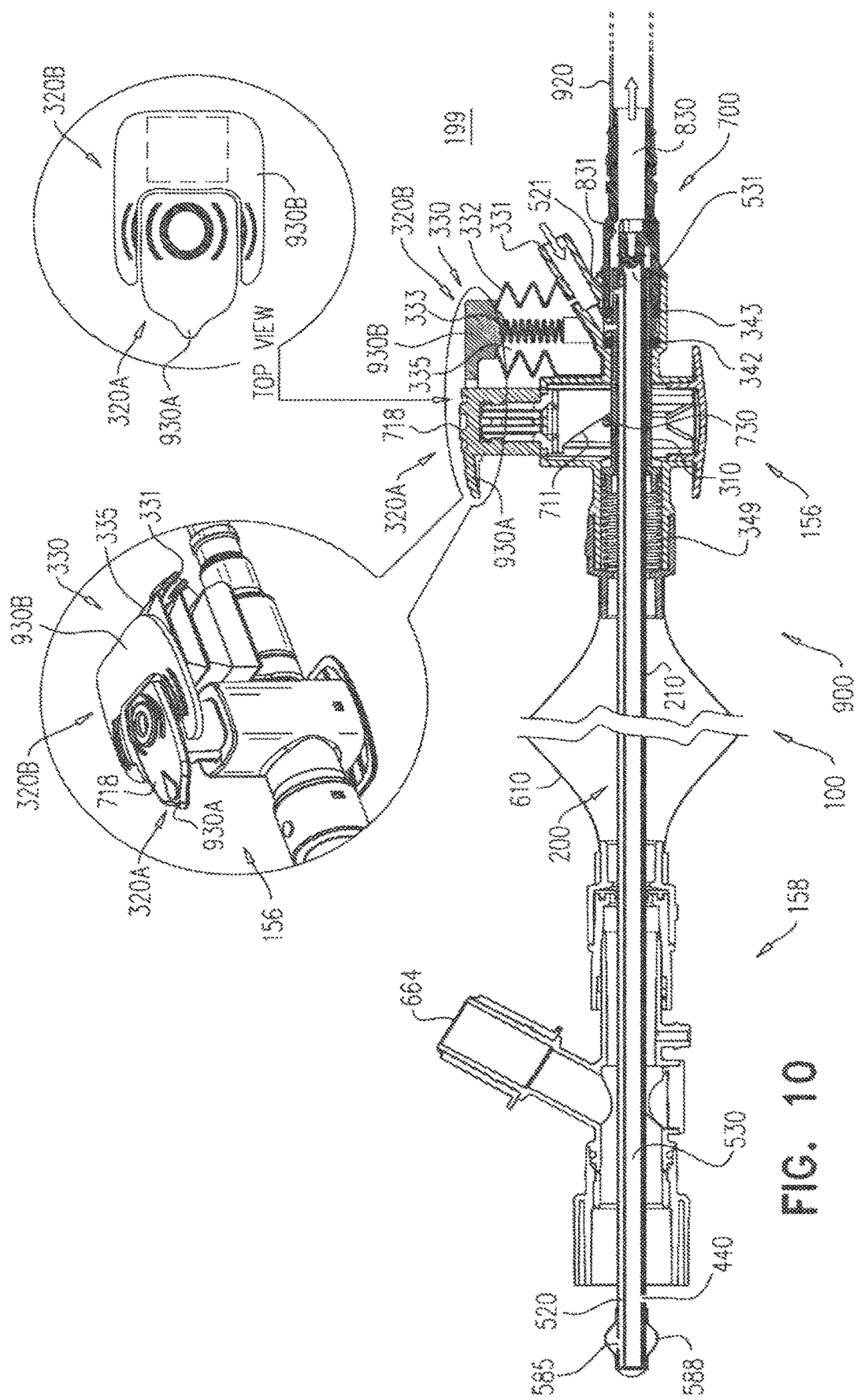
FIG. 10 is a schematic cross-sectional illustration of another closed suction cleaning system in a first fluid-control state, in accordance with an application of the present invention.
Figure 11A:
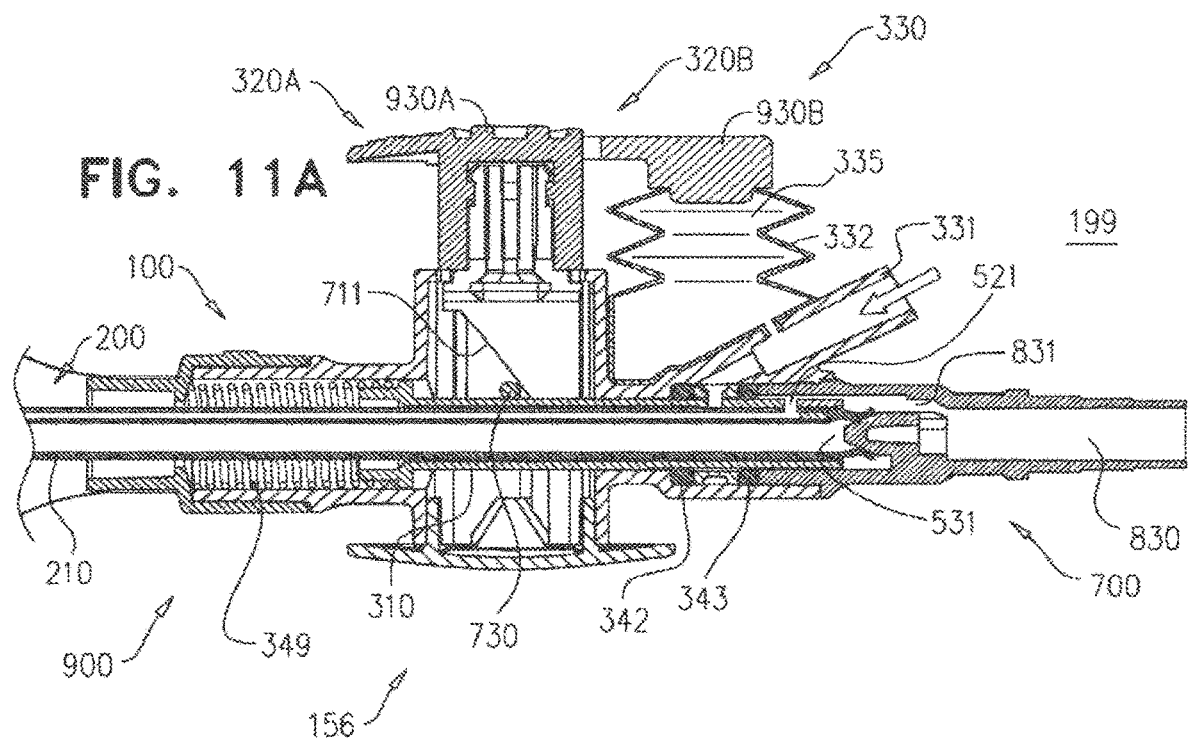
FIGS. 11A-C are schematic cross-sectional illustrations of a portion of the closed suction cleaning system of FIG. 10 in the first fluid-control state, a second fluid-control state, and a third fluid-control state, respectively, in accordance with an application of the present invention.
Figure 11B:
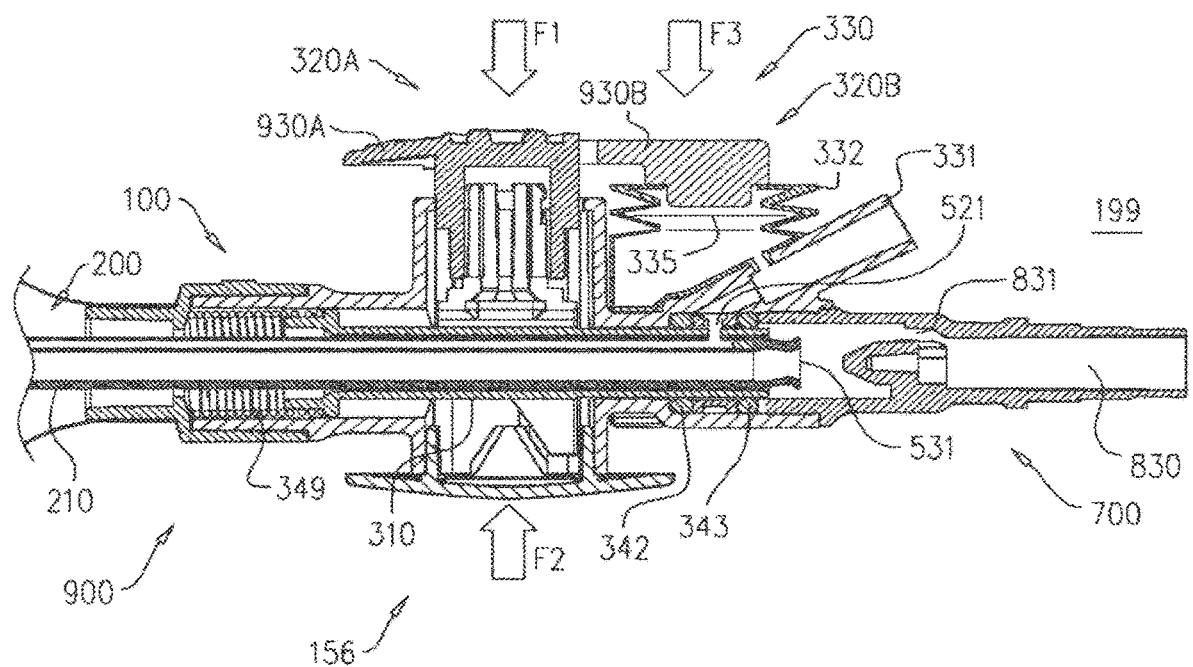

Reference is now made to FIG. 10, which is a schematic cross-sectional illustration of a closed suction cleaning system 900 in a first fluid-control state, in accordance with an application of the present invention. Reference is also made to FIGS. 11A-B, which are schematic cross-sectional illustrations of a portion of closed suction cleaning system 900 in the first fluid-control state and a second fluid-control state, respectively, in accordance with an application of the present invention. Closed suction cleaning system 900 is one implementation of closed suction cleaning system 100, described hereinabove with reference to FIGS. 1-3, and, except as described hereinbelow, may implement any of the features of closed suction cleaning system 400 described hereinabove with reference to FIGS. 4 and 5A-C. For illustrative purposes, inflatable element 588 is shown inflated in FIG. 10, even though the inflatable element is in practice not inflated in the first fluid-control state shown in FIG. 10, as described herein.

In this configuration, input module 156 comprises a first mechanical user control element 320A, which is configured to mechanically and non-electrically set the fluid-control states of flow regulator 700. First mechanical user control element 320A is configured to assume at least first and second configurations, such as first and second spatial positions, respectively. For some applications, as shown, first mechanical user control element 320A comprises a first user control button 930A.

In this configuration, input module 156 further comprises a second mechanical user control element 320B, which is configured (a) to assume at least first and second configurations, such as first and second spatial positions, and (b) to mechanically and non-electrically increase pressure in the interior of inflation chamber 335 during a transition of second mechanical user control element 320B from its first configuration to its second configuration. In these applications, inflation chamber 335 functions as a compression pump. For some applications, as shown, second mechanical user control element 320B comprises a second user control button 930B.

For some applications, input module 156 is arranged such that:
when first mechanical user control element 320A is in its first configuration (e.g., spatial position), as shown in FIGS. 10 and 11A, flow regulator 700 is in the first fluid-control state, in which flow regulator 700 blocks fluid communication between suction source 601 and distal suction orifices 440, and
when first mechanical user control element 320A is in its second configuration (e.g., spatial position), as shown in FIG. 11B, flow regulator 700 is in the second fluid-control state, in which flow regulator 700 (a) connects suction source 601 and distal suction orifices 440 in fluid communication, and (b) connects the interior of inflation chamber 335 and an interior of inflatable element 588 in fluid communication to inflate inflatable element 588.

For some applications, as labeled in FIG. 11B, a healthcare worker applies:
a first force F1 to first mechanical user control element 320A (such as to first user control button 930A thereof),
a third force F3 to second mechanical user control element 320B (such as to second user control button 930B thereof), and
a second force F2, directed toward the first and the third forces F1 and F3, to the opposite side of input module 156 from first and second user control elements 320A and 320B.

For some applications, first and second mechanical user control elements 320A and 320B (e.g., first and second user control buttons 930A and 930B) are arranged side-by-side. For some applications, first and second mechanical user control elements 320A and 320B (e.g., first and second user control buttons 930A and 930B) are arranged such that a portion of one of the mechanical user control elements (e.g., control buttons) at least partially (i.e., partially or entirely) surrounds the other user control element (e.g., control button). For example, second mechanical user control element 320B (e.g., second user control button 930B) may at least partially surround at least two sides of first mechanical user control element 320A (e.g., first user control button 930A), such as at least three sides (e.g., three entire sides) of first mechanical user control element 320A (e.g., first user control button 930A), as shown in FIG. 10. Alternatively, for example, first mechanical user control element 320A (e.g., first user control button 930A) may at least partially surround at least two sides of second mechanical user control element 320B (e.g., second user control button 930B), such as at least three sides (e.g., three entire sides) of second mechanical user control element 320B (e.g., second user control button 930B) (configurations not shown). In these side-by-side arrangements, a closest distance between first and second mechanical user control elements 320A and 320B (e.g., first and second user control buttons 930A and 930B) is typically at least 0.1 mm, no more than 2 mm (e.g., no more than 1 mm), and/or between 0.1 mm and 2 mm (e.g., 1 mm).

Providing the control elements side-by-side may enable both (a) ergonomically-convenient simultaneous pressing of both control elements, such as to transition flow regulator 700 from the first fluid-control state to the second fluid-control state, and (b) pressing of only first mechanical user control element 320A (e.g., first user control button 930A) to transition flow regulator 700 from the first fluid-control state to a third fluid-control state, such as described hereinbelow.

Figure 11C:
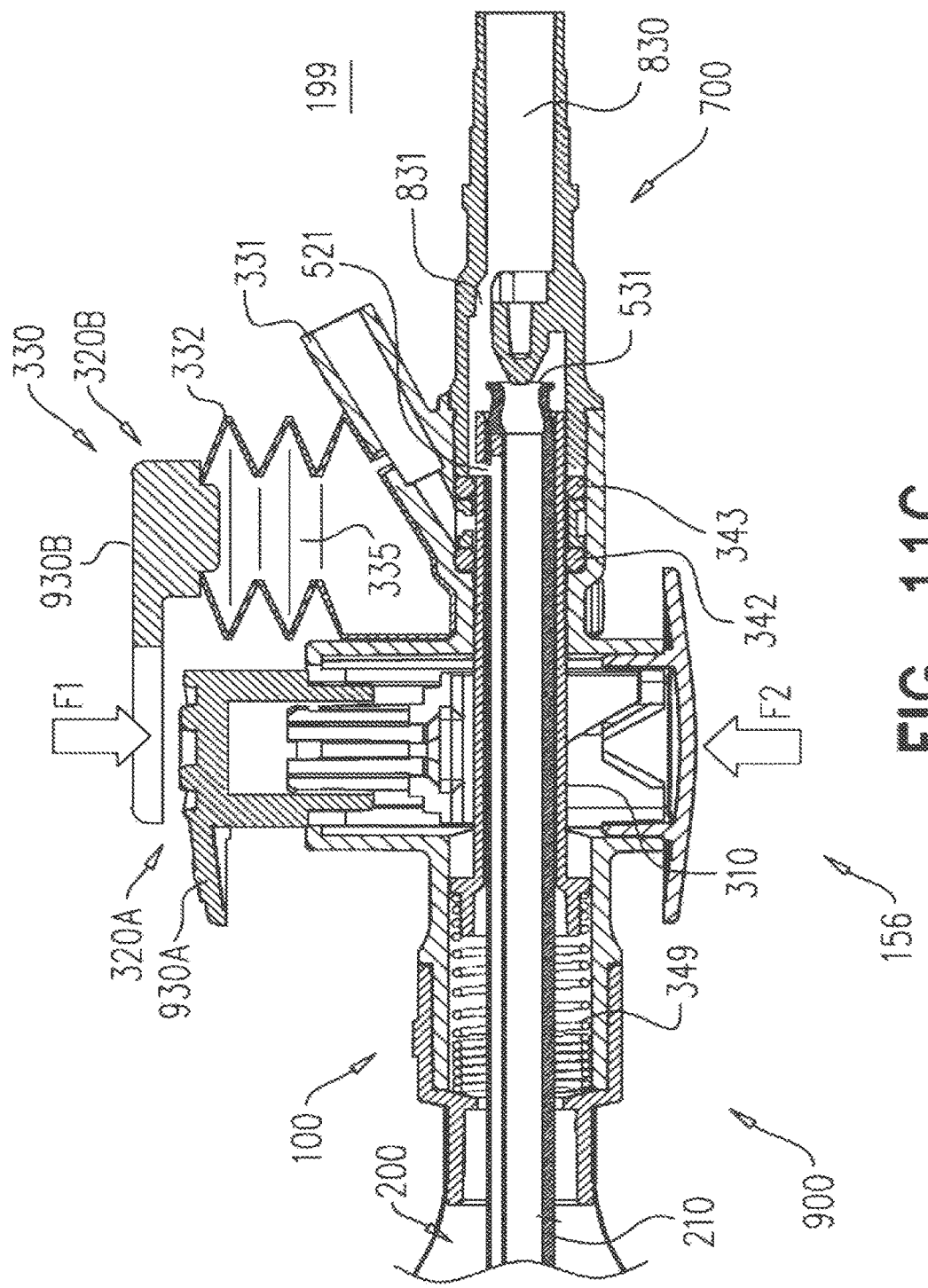

Reference is now made to FIG. 11C, which is a schematic cross-sectional illustration of a portion of closed suction cleaning system 900 in a third fluid-control state, in accordance with an application of the present invention. For some applications, cleaning system 900 may also be used for suctioning the trachea outside of and distal to ventilation tube 160, typically when flow regulator 700 is in one of the following states:

as shown in FIG. 11B, the second fluid-control state, in which suction source 601 and distal suction orifices 440 are in fluid communication (and inflatable element 588 is inflated), or as shown in FIG. 11C, the third, intermediate fluid-control state, between the first and the second fluid-control states, in which (a) suction source 601 and distal suction orifices 440 are in fluid communication with one another, and (b) the interior of inflation chamber 335 and the interior of inflatable element 588 are not in fluid communication with one another, and inflatable element 588 is thus not inflated.

For some applications, flow regulator 700 is configured to assume the third, intermediate fluid-control state when:

first mechanical user control element 320A (e.g., first user control button 930A) is in a third, intermediate configuration (e.g., spatial position), as shown in FIG. 11C, between its first configuration (e.g., spatial position), as shown in FIG. 11A, and its second configuration (e.g., spatial configuration), as shown in FIG. 11B, and second mechanical user control element 320B (e.g., second user control button 930B) is in its first configuration (e.g., spatial position), as shown in FIG. 11C.

For some applications, when first mechanical user control element 320A (e.g., first user control button 930A) is in the third, intermediate configuration and flow regulator 700 is in the third, intermediate fluid-control state:

inflation inlet 521 is not in fluid communication with outlet 337 of inflation chamber 335; typically, inflation inlet 521 is in fluid communication with suction port 830, such as via at least one suction channel 831, to maintain inflatable element 588 deflated, as shown in FIG. 11C (alternatively, inflation inlet 521 is axially aligned with a wall of input module housing 310, e.g., slightly proximal to (i.e., to the right of, in FIG. 11B) the position of inflation inlet 521 shown in FIG. 11B (and thus slightly proximal to outlet 337), because catheter main body 210 is positioned slightly proximal to (i.e., to the right of, in FIG. 11B) the position shown in FIG. 11B), and as shown in FIG. 11C, proximal suction inlet 531 is in fluid communication with suction port 830, such as via at least one suction channel 831, e.g., with proximal suction inlet 531 disposed slightly proximal to (i.e., to the right of, in FIG. 11B) the position of proximal suction inlet 531 shown in FIG. 11B, but not so proximal (e.g., far to the right in FIG. 11B) as to form a seal with suction sealer 375.

Flow regulator 700 may have any of the features thereof described hereinabove with reference to FIG. 5C, *mutatis mutandis*.

For other applications (configuration not shown), flow regulator 700 is configured to assume the third, intermediate fluid-control state when:

first mechanical user control element 320A (e.g., first user control button 930A) is in the third, intermediate configuration (e.g., spatial position), as shown in FIG. 11C, and second mechanical user control element 320B (e.g., second user control button 930B) is in a third, intermediate configuration (e.g., spatial position), between its first configuration (e.g., spatial position), as shown in FIG. 11A, and its second configuration (e.g., spatial configuration), as shown in FIG. 11B (configuration not shown).

For still other applications (configuration not shown), flow regulator 700 is configured to assume the third, intermediate fluid-control state when:

first mechanical user control element 320A (e.g., first user control button 930A) is in its second configuration (e.g., spatial position), as shown in FIG. 11B, and second mechanical user control element 320B (e.g., second user control button 930B) is in its first configuration (e.g., spatial position), as shown in FIG. 11A.

For some applications, inflation chamber 335 transitions from a lower level of compression to a higher level of compression during the transition of second mechanical user control element 320B from its first configuration to its second configuration. For some of these applications, input module 156 is configured to elastically bias inflation chamber 335 toward the lower level of compression. For some applications, inflation chamber 335 (e.g., at least one wall 332 of inflation chamber 335) is elastically biased toward the lower level of compression. For example, the at least one wall of inflation chamber 335 may be accordion-shaped and/or the chamber walls comprise an elastic material, such as silicon, rubber, or polyurethane. In some embodiments, substantially no friction needs to be overcome during expansion of inflation chamber 335. Alternatively or additionally, inflation module 330 (such as inflation chamber 335) comprises a distinct elastic element 333 (e.g., a spring) that is arranged to bias inflation chamber 335 toward the lower level of compression. Alternatively or additionally, second mechanical user control element 320B is elastically biased toward the lower level of compression (and to the first configuration), for example by a spring 349. In any event, typically, when second mechanical user control element 320B is released, inflation chamber 335 expands. In other words, input module 156 is biased to assume the first configuration and first fluid-control state when in a resting state, such that inflation chamber 335 is in an expanded state when input module 156 is in the resting state.

For some applications, first mechanical user control element 320A comprises user control handle 718, the movement of which includes a component perpendicular to the associated axial motion of catheter main body 210. First mechanical user control element 320A translates the movement of user control handle 718 into axial motion of catheter main body 210. For example, first mechanical user control element 320A may comprise side projection element 730 attached to catheter main body 210, and engaging element 711 that has a diagonal face which engages side projection element 730, such that when engaging element 711 moves down, it pushes side projection element 730 sideways and thus imparts axial motion to catheter main body 210.

Although the fluid-control states of flow regulator 700 of input module 156 are sometimes characterized hereinabove as "first," "second," and "third," these ordinal numbers do not necessarily imply a particular order of activation during use of cleaning system 100 unless explicitly stated. In addition, input module 156 may have activation states in addition to those described herein, which may be activated before, after, or temporarily between the states described herein. The ordinal numbers of the states recited in claims do not necessarily correspond to the ordinal numbers of the states described hereinabove in the specification.

In the description and claims of the present application, each of the verbs, "comprise," "include" and "have," and conjugates thereof, are used to indicate that the object or objects of the verb are not necessarily a complete listing of members, components, elements or parts of the subject or subjects of the verb. The articles "a" and "an" are used herein to refer to one or to more than one (i.e., to at least one) of the grammatical object of the article. By way of example, "an element" means one element or more than one element. The term "including" is used herein to mean, and is used interchangeably with, the phrase "including but not limited to." The term "or" is used herein to mean, and is used interchangeably with, the term "and/or," unless context clearly indicates otherwise. The term "such as" is used herein to mean, and is used interchangeably with, the phrase "such as but not limited to."

All publications, patent applications, patents, and other references mentioned herein are incorporated by reference in their entirety. In case of conflict, the present patent specification, including definitions, will prevail. In addition, the materials, methods, and examples are illustrative only and not intended to be limiting.

For brevity, some explicit combinations of various features are not explicitly illustrated in the figures and/or described. It is now disclosed that any combination of the method or device features disclosed herein can be combined in any manner including any combination of features—any combination of features can be included in any embodiment and/or omitted from any embodiments.

The scope of the present invention includes embodiments described in the following applications, which are assigned to the assignee of the present application and are incorporated herein by reference. In an embodiment, techniques and apparatus described in one or more of the following applications are combined with techniques and apparatus described herein. It is noted that the phrase "fluid-control state" used herein may, for some applications, correspond in some respects to the phrases "mode," "activation mode," and/or "operating mode" referred to in the following applications (although many of the configurations of these states described herein differ in at least some respects from the configurations of the modes described in the following applications). It is also noted that the phrase "mechanical user control element" used herein may, for some applications, correspond in some respects to the word "switch," referred to in the following applications (although many of the configurations of these states described herein differ in at least some respects from the configurations of the modes described in the following applications):

PCT Publication WO/2012/131626 to Einav et al.
GB 2482618 A to Einav et al.;
UK Application GB 1119794.4, filed Nov. 16, 2011;
U.S. Provisional Application 61/468,990, filed Mar. 29, 2011;
U.S. Provisional Application 61/473,790, filed Apr. 10, 2011;
U.S. Provisional Application 61/483,699, filed May 8, 2011;
U.S. Provisional Application 61/496,019, filed Jun. 12, 2011;
U.S. Provisional Application 61/527,658, filed Aug. 26, 2011;
U.S. Provisional Application 61/539,998, filed Sep. 28, 2011;
U.S. Provisional Application 61/560,385, filed Nov. 16, 2011;
U.S. Provisional Application 61/603,340, filed Feb. 26, 2012;
U.S. Provisional Application 61/603,344, filed Feb. 26, 2012;
U.S. Provisional Application 61/609,763, filed Mar. 12, 2012;
U.S. Provisional Application 61/613,408, filed Mar. 20, 2012;
U.S. Provisional Application 61/635,360, filed Apr. 19, 2012;
U.S. Provisional Application 61/655,801, filed Jun. 5, 2012;
U.S. Provisional Application 61/660,832, filed Jun. 18, 2012;
U.S. Provisional Application 61/673,744, filed Jul. 20, 2012;
PCT Publication WO 2013/030821 to Zachar et al.;
U.S. Pat. No. 8,999,074 to Zachar et al;
UK Application 1600233.9, filed Jan. 6, 2016;
U.S. Provisional Application 62/287,223, filed Jan. 26, 2016; and
U.S. Provisional Application 62/319,640, filed Apr. 7, 2016.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a tracheal ventilation tube and a suction source, the apparatus comprising:
   (A) a cleaning catheter, which (a) is insertable into the ventilation tube, (b) is shaped so as to define one or more distal suction orifices, and (c) which comprises:
      (i) an elongate, flexible, tubular catheter main body; and
      (ii) an inflatable element, which is mounted to the catheter main body at a location within 3 cm of at least one of the one or more distal suction orifices; and
   (B) an input module, which is coupled to the cleaning catheter, and comprises:
      (i) an inflation module, which comprises an inflation chamber separate from the suction source;
      (ii) a flow regulator, which (a) is shaped so as to define a suction port coupleable in fluid communication with the suction source, and (b) is configured to assume at least first and second fluid-control states; and
      (iii) a mechanical user control element, which is configured (a) to mechanically and non-electrically set the fluid-control states of the flow regulator, (b) to assume at least first and second configurations, and (c) to mechanically and non-electrically increase pressure in an interior of the inflation chamber during at least a portion of a transition of the mechanical user control element from the first configuration to the second configuration,
   wherein the input module is arranged such that:
   at least when the mechanical user control element is in the first configuration, the flow regulator is in the first fluid-control state, in which the flow regulator (a) blocks fluid communication between the suction source and the distal suction orifices and (b) connects the suction source and an interior of the inflatable element in fluid communication to deflate the inflatable element,
   at least when the mechanical user control element is in the second configuration, the flow regulator is in the second fluid-control state, in which the flow regulator (a) connects the suction source and the distal suction orifices in fluid communication, (b) connects the interior of the inflation chamber and an interior of the inflatable element in fluid communication to inflate the inflatable element, and (c) does not connect the suction source and the interior of the inflatable element in fluid communication, and the flow regulator is (a) not in the first fluid-control state when the mechanical user control element is in the second configuration, and (b) not in the second fluid control state when the mechanical user control element is in the first configuration,
   wherein the catheter main body comprises a proximal-most input portion, which is disposed within and axially slidable or axially fixed with respect to the input module.

2. The apparatus according to claim 1, wherein the mechanical user control element is configured to mechanically and non-electrically increase the pressure in the interior of the inflation chamber during an entirely of the transition of the mechanical user control element from the first configuration to the second configuration.

3. The apparatus according to claim 1, wherein the input module is configured such that during the at least a portion of the transition of the mechanical user control element from the first configuration to the second configuration, before the flow regulator assumes the second fluid-control state, a volume of the interior of the inflation chamber decreases by between 10% and 90%.

4. The apparatus according to claim 1, wherein the mechanical user control element is configured to mechanically and non-electrically increase the pressure in the interior of the inflation chamber during motion of the mechanical user control element while the flow regulator is in the second fluid-control state.

5. The apparatus according to claim 1, wherein the suction port is coupled in fluid communication with the suction source.

6. The apparatus according to claim 1, wherein the input module further comprises a user signal generator, which is configured to generate a user signal during or upon deflation of the inflatable element.

7. The apparatus according to claim 1, wherein the inflation chamber has a volume of between 1 and 10 cc when the mechanical user control element is in the first configuration.

8. The apparatus according to claim 1, wherein when the mechanical user control element is in the second configuration, the inflation chamber has a volume of at least 1 cc less than when the mechanical user control element is in the first configuration.

9. The apparatus according to claim 1, wherein the mechanical user control element is biased toward the first configuration.

10. The apparatus according to claim 1, wherein the cleaning catheter further comprises one or more suction lumens arranged along the catheter main body, and wherein the flow regulator, when in the second fluid-control state, connects in fluid communication the suction source and the distal suction orifices via the one or more suction lumens.

11. The apparatus according to claim 1, wherein the inflatable element comprises a balloon.

12. The apparatus according to claim 1, wherein the inflatable element is mounted to the catheter main body is within 5 cm of a distal end of the catheter main body.

13. The apparatus according to claim 1, wherein the inflatable element has a greatest outer diameter of between 6 and 12 mm when inflated at 1 bar above atmospheric pressure and unconstrained.

14. The apparatus according to claim 1, wherein the apparatus is for use with a ventilator, and wherein the apparatus further comprises a tube-connector assembly, which is configured to couple the ventilation tube in fluid communication with the ventilator, in a substantially airtight manner.

15. The apparatus according to claim 1, wherein the first and the second configurations are first and second spatial positions, respectively, and wherein the mechanical user control element is configured to assume at least the first and the second spatial positions.

16. The apparatus according to claim 15, wherein the mechanical user control element is arranged to move between first and second spatial end-points, and wherein the first and the second spatial positions correspond with the first and the second spatial end-points, respectively.

17. The apparatus according to claim 1, wherein the flow regulator is configured to assume a third, intermediate fluid-control state, between the first and the second fluid-control states, in which (a) the suction source and the distal suction orifices are in fluid communication with one another, and (b) the interior of the inflation chamber and the interior of the inflatable element are not in fluid communication with one another, and wherein the flow regulator is configured to assume the third, intermediate fluid-control state when the mechanical user control element is in a third, intermediate configuration between the first configuration and the second configuration.

18. The apparatus according to claim 1, wherein the inflation module comprises a one-way air inlet valve, which is arranged to allow air to flow into the inflation chamber during at least a portion of a transition of the mechanical user control element from the second configuration to the first configuration.

19. The apparatus according to claim 18, wherein the one-way air inlet valve is configured to generate a sound signal during at least a portion of a period of fluid flow into the inflation chamber.

20. The apparatus according to claim 1, wherein the mechanical user control element is configured to increase the pressure in the interior of the inflation chamber by mechanically and non-electrically compressing the inflation chamber during the at least a portion of the transition of the mechanical user control element from the first configuration to the second configuration.

* * * * *